US012369925B2

(12) United States Patent
Clevett et al.

(10) Patent No.: US 12,369,925 B2
(45) Date of Patent: Jul. 29, 2025

(54) FOLDING SURGICAL GUIDE AND METHODS OF REPAIR

(71) Applicant: ARTHREX, INC., Naples, FL (US)

(72) Inventors: James Tyler Clevett, Bonita Springs, FL (US); Nicholas Clement Mealey, Marshallville, OH (US)

(73) Assignee: ARTHREX, INC., Naples, FL (US)

( * ) Notice: Subject to any disclaimer, the term of this patent is extended or adjusted under 35 U.S.C. 154(b) by 410 days.

(21) Appl. No.: 18/155,136

(22) Filed: Jan. 17, 2023

(65) Prior Publication Data
US 2023/0225745 A1 Jul. 20, 2023

Related U.S. Application Data

(60) Provisional application No. 63/300,683, filed on Jan. 19, 2022.

(51) Int. Cl.
*A61B 17/15* (2006.01)
*A61B 17/00* (2006.01)
*A61B 17/02* (2006.01)
*A61B 17/16* (2006.01)
*A61B 17/17* (2006.01)
(Continued)

(52) U.S. Cl.
CPC .... *A61B 17/151* (2013.01); *A61B 2017/0046* (2013.01); *A61B 2017/00477* (2013.01); *A61B 17/02* (2013.01); *A61B 17/1684* (2013.01); *A61B 17/1746* (2013.01); *A61B 17/1778* (2016.11); *A61B 2090/08021* (2016.02); *A61F 2/4657* (2013.01); *A61F 2002/4659* (2013.01);
(Continued)

(58) Field of Classification Search
CPC . A61B 17/15; A61B 17/1684; A61B 17/1778; A61B 17/151; A61B 17/02; A61B 17/17; A61B 17/1746; A61B 2017/0046; A61B 2017/00477; A61B 2090/033; A61B 2090/08021; A61F 2/46; A61F 2/4657; A61F 2002/4658; A61F 2002/4659; A61F 2002/4668; A61F 2002/4687; G01B 5/025; G01B 5/08; G01B 5/12
USPC .......................................................... 606/82
See application file for complete search history.

(56) References Cited

U.S. PATENT DOCUMENTS 2,841,148 A * 7/1958 Kadavy .............. A61B 17/0293
606/148
5,947,895 A * 9/1999 Warner .............. A61B 17/0218
606/198
(Continued)

FOREIGN PATENT DOCUMENTS

EP 1442715 8/2004
FR 2997621 5/2014

OTHER PUBLICATIONS

International Preliminary Report on Patentability for International Application No. PCT/US2023/060719 mailed Aug. 2, 2024.
(Continued)

*Primary Examiner* — Marcela I. Shirsat
(74) *Attorney, Agent, or Firm* — Carlson, Gaskey & Olds, P.C.

(57) ABSTRACT

This disclosure relates to surgical devices and methods. The disclosed surgical device and method may be used to resect, cut or otherwise remove tissue during an orthopaedic procedure. The surgical device may be reconfigured to reduce a size of the surgical device during placement in the patient.

20 Claims, 20 Drawing Sheets

(51) Int. Cl.
*A61B 90/00* (2016.01)
*A61F 2/46* (2006.01)
*G01B 5/02* (2006.01)
*G01B 5/08* (2006.01)

(52) U.S. Cl.
CPC ...... *A61F 2002/4687* (2013.01); *G01B 5/025* (2013.01); *G01B 5/08* (2013.01)

(56) References Cited

U.S. PATENT DOCUMENTS

| | | | |
|---|---|---|---|
| 6,083,154 A * | 7/2000 | Liu | A61B 17/0293 |
| | | | 600/234 |
| 7,699,847 B2 | 4/2010 | Sheldon et al. | |
| 8,388,528 B2 * | 3/2013 | Rioux | A61B 17/0293 |
| | | | 600/233 |
| 8,758,235 B2 * | 6/2014 | Jaworek | A61B 17/0218 |
| | | | 600/206 |
| 9,320,422 B1 * | 4/2016 | Makhlouf | A61B 17/02 |
| 10,413,416 B2 | 9/2019 | Boileau et al. | |
| 11,116,522 B2 | 9/2021 | Burt | |
| 2013/0261629 A1 | 10/2013 | Anthony et al. | |
| 2016/0374698 A1 | 12/2016 | Kurtz | |
| 2020/0405330 A1 | 12/2020 | Bonin, Jr. et al. | |
| 2021/0228217 A1 | 7/2021 | Adkison | |

OTHER PUBLICATIONS

International Search Report for International Application No. PCT/US2023/060719 mailed May 8, 2023.

* cited by examiner

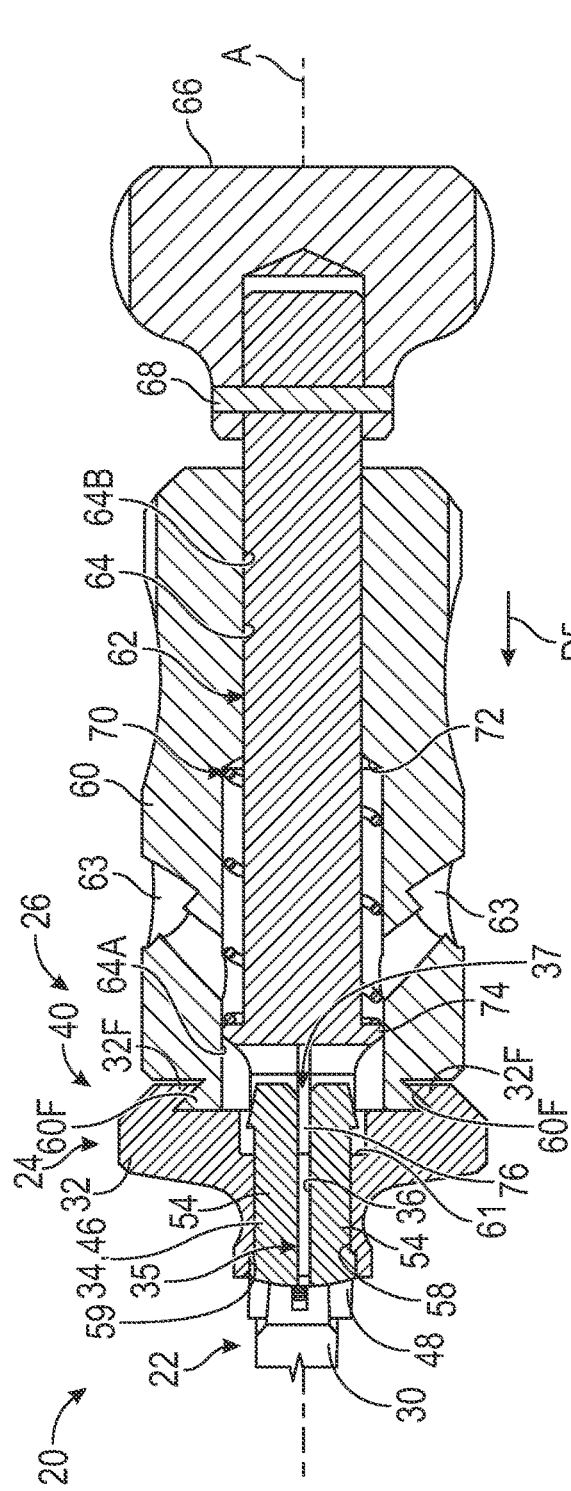
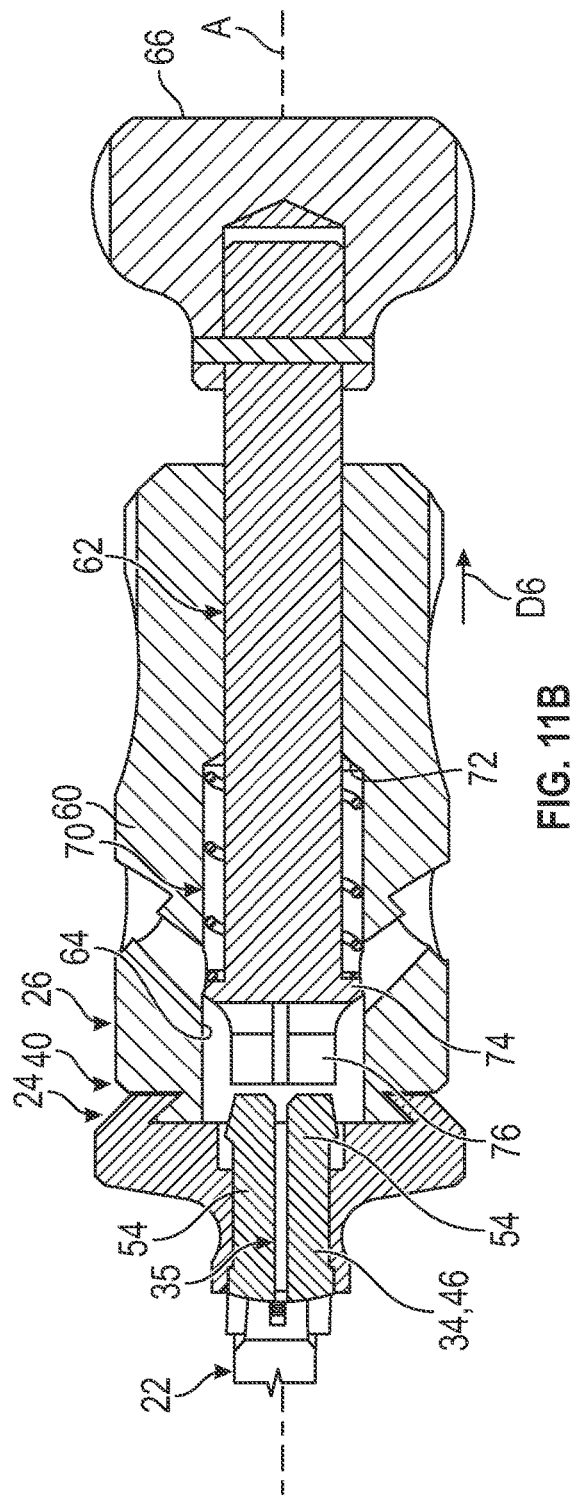
FIG. 11A
FIG. 11B

FOLDING SURGICAL GUIDE AND METHODS OF REPAIR

CROSS-REFERENCE TO RELATED APPLICATION

The present disclosure claims benefit of U.S. Provisional Application No. 63/300,683 filed Jan. 19, 2022.

BACKGROUND

This disclosure relates to orthopaedic procedures and, more particularly, to systems and methods for repairing bone defects and restoration of functionality to a joint.

Many bones of the human musculoskeletal system include articular surfaces. The articular surfaces articulate relative to other bones to facilitate different types and degrees of joint movement. The articular surfaces can erode (i.e., experience bone loss) over time due to repeated use or wear or can fracture as a result of a traumatic impact. These types of bone defects can cause joint instability and pain.

Bone deficiencies may occur along the articular surfaces of the bone. Some techniques utilize a bone graft and/or implant to repair a defect in the bone. The bone may be resected to remove the defect and prepare the bone for receiving the bone graft or implant.

SUMMARY

This disclosure relates to surgical devices and methods. The surgical device may be used during methods for repairing bone defects. The surgical devices described herein may include a surgical guide utilized to position a surgical instrument for resecting, cutting or otherwise removing tissue at a surgical site.

A surgical guide for an orthopaedic procedure of the present disclosure may include a shield including first and second shield portion and a housing including a first housing portion pivotably coupled to a second housing portion. The first and second shield portions may be coupled to the respective first and second housing portions. The first and second shield portions may be moveable relative to each other between a folded position and a deployed position in response to relative rotation between the first and second housing portions about an axis. The first and second shield portions may be configured to bound a work area in the deployed position. The work area may be dimensioned to receive a portion of bone. The housing may include a resection slot extending from the work area.

A kit for an orthopaedic procedure of the present disclosure may include a cutting instrument including cutting teeth and a surgical guide. The surgical guide may include a shield configured to bound a work area in a deployed position. The work area may be dimensioned to receive a portion of bone. A housing may include first and second housing portions coupled to respective end portions of the shield. The first and second housing portions may be pivotable relative to each other about an axis to move the shield between a folded position and the deployed position. The housing may include a resection slot extending along a reference plane that intersects the work area. The shield may be configured to block movement of the cutting instrument along the reference plane.

A method of performing an orthopaedic procedure of the present disclosure may include situating a surgical guide at a surgical site, and moving the surgical guide from a folded position to a deployed position at the surgical site. The surgical guide may include a shield configured to bound a work area in the deployed position and a housing including first and second housing portions coupled to respective end portions of the shield. The second housing portion may be pivotable relative to an axis of the first housing portion to move the shield between the folded position and the deployed position. The housing may include a resection slot extending from the work area. The method may include positioning a bone in the work area such that the shield at least partially surrounds a periphery of the bone. The method may include inserting a cutting instrument through the resection slot and into the work area to resect the bone.

The various features and advantages of this disclosure will become apparent to those skilled in the art from the following detailed description. The drawings that accompany the detailed description can be briefly described as follows.

BRIEF DESCRIPTION OF THE DRAWINGS

FIGS. 11A-11B illustrate sectional views of the surgical guide with the actuation member in a locked position and an unlocked position.

Like reference numbers and designations in the various drawings indicate like elements.

DETAILED DESCRIPTION

Figure 1:
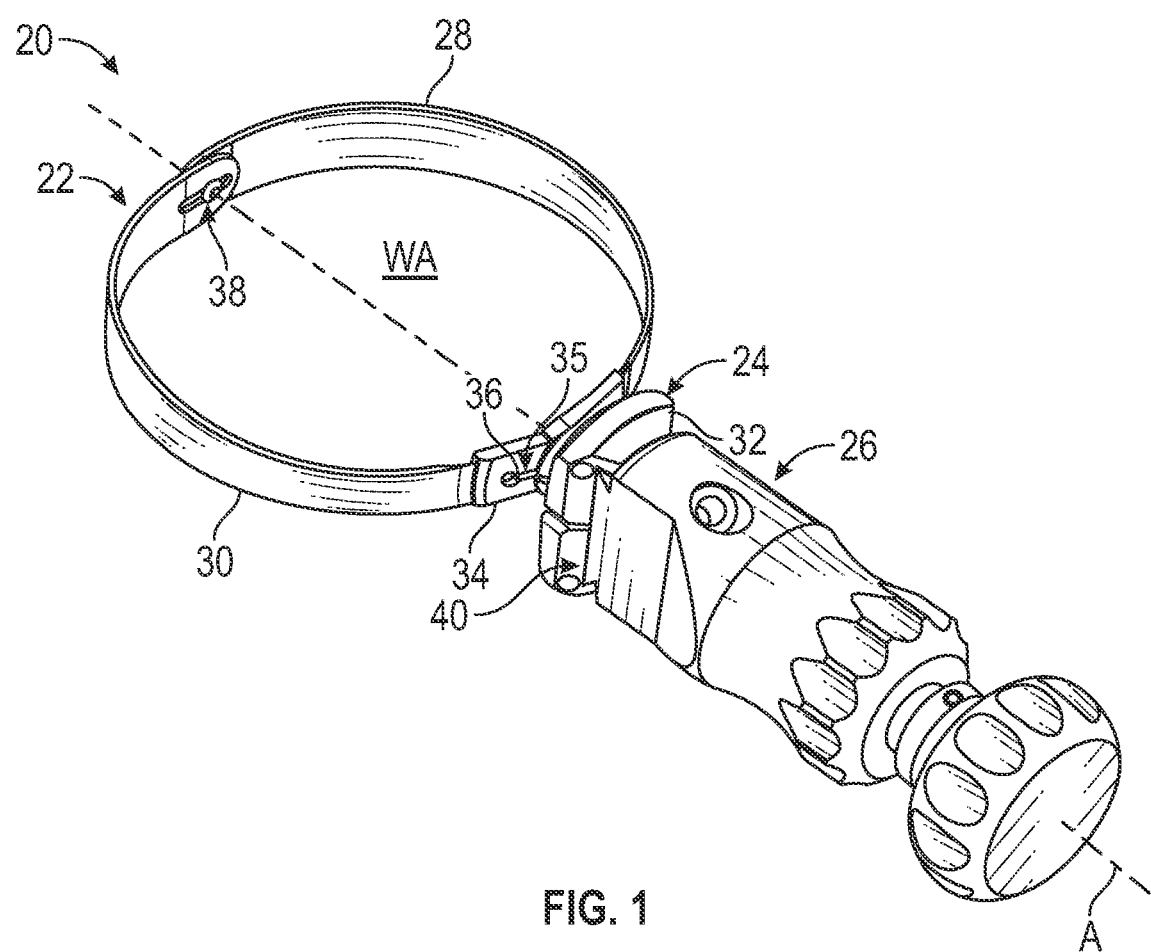
FIG. 1 illustrates a perspective view of a surgical guide in a deployed position.

This disclosure relates to orthopaedic procedures, such as a total shoulder arthroplasty (TSA). A TSA is a procedure which may include a bony resection of the humeral head at an inclination and version angle that may closely approximate the inclination and version angle of the pre-diseased humeral head. The shoulder joint may be accessed through a window or passage in the subscapularis. A cutting instrument such as a sagittal or reciprocating saw may be utilized to perform the resection. The subscapularis and surrounding soft tissue may be at risk of damage through contact with the saw.

A surgical guide may be utilized to orient the cutting instrument. The surgical guide may be reconfigured between a deployed position and a folded position to reduce a size of the surgical guide during placement in a patient. The surgical guide may be compactly passed through the subscapularis window or rotator cuff interval (e.g., supraspinatus-subscapularis gap) prior to unfolding a shield of the guide. The shield may be unfolded to fully or at least partially encircle the humeral head at the resection plane. The shield may be dimensioned to sit atop the cuff insertion points to guide an anatomic head resection. A relatively small saw blade may then be passed into a resection slot or other guide passage in the guide to execute the head resection while the shield of the guide serves to shield the surrounding tissue including the rotator cuff axillary nerve. The guide may then be folded back to its compact form to be removed from the site.

A surgical guide for an orthopaedic procedure of the present disclosure may include a shield including first and second shield portion and a housing including a first housing portion pivotably coupled to a second housing portion. The first and second shield portions may be coupled to the respective first and second housing portions. The first and second shield portions may be moveable relative to each other between a folded position and a deployed position in response to relative rotation between the first and second housing portions about an axis. The first and second shield portions may be configured to bound a work area in the deployed position. The work area may be dimensioned to receive a portion of bone. The housing may include a resection slot extending from the work area.

In a further implementation, the first shield portion may be pivotably coupled to the second shield portion at a connection. The connection may be spaced apart from the housing.

In a further implementation, the first and second shield portions may cooperate with the housing to encircle the work area in the deployed position.

In a further implementation, a handle may be releasably secured to the housing along an interface.

In a further implementation, the resection slot may extend between the interface and the work area.

In a further implementation, the first housing portion may include a first flange extending from a first body. The second housing portion may include a second flange extending from a second body. The first and second flanges may be coupled to the respective first and second shield portions.

In a further implementation, the first body may include a passageway extending along the resection slot. The second body may include a pair of lock members configured to deflect inwardly in response to being inserted in the passageway and then to deflect outwardly to lock the second body in the first body.

In a further implementation, a handle may be releasably secured to the housing along an interface. The handle may include an actuation member moveable between first and second positions relative to the interface. The actuation member may be configured to engage the lock members in the first position to lock the handle to the housing and may be configured to disengage the lock members in the second position such that the handle may be releasable from the housing.

In a further implementation, a first slot may extend through the first housing portion. A second slot may extend through the second housing portion. The first and second slots may be substantially aligned in the deployed position to establish the resection slot.

In a further implementation, the resection slot may be established along the axis.

In a further implementation, the first slot ma be transverse to the second slot in response to moving the shield between the deployed position and the folded position.

In a further implementation, the shield may be flexible such that the first and second shield portions may be conformable to a periphery of a portion of bone captured in the work area.

A kit for an orthopaedic procedure of the present disclosure may include a cutting instrument including cutting teeth and a surgical guide. The surgical guide may include a shield configured to bound a work area in a deployed position. The work area may be dimensioned to receive a portion of bone. A housing may include first and second housing portions coupled to respective end portions of the shield. The first and second housing portions may be pivotable relative to each other about an axis to move the shield between a folded position and the deployed position. The housing may include a resection slot extending along a reference plane that intersects the work area. The shield may be configured to block movement of the cutting instrument along the reference plane.

In a further implementation, the shield may include a first shield portion pivotably coupled to a second shield portion at a connection. The connection may be spaced apart from the housing.

In a further implementation, a first slot may extend through the first housing portion. A second slot may extend through the second housing portion. The first and second slots may be substantially aligned along the reference plane in the deployed position to establish the resection slot.

In a further implementation, a handle may be releasably secured to the first housing portion along an interface. The handle may include an actuation member moveable between first and second positions relative to the interface. The actuation member may be configured to engage the second housing portion in the first position to lock the handle to the housing to block access to an entrance to the resection slot. The actuation member may be configured to disengage the second housing portion in the second position such that the handle may be releasable from the first housing portion to provide access to the entrance to the resection slot.

A method of performing an orthopaedic procedure of the present disclosure may include situating a surgical guide at a surgical site, and moving the surgical guide from a folded position to a deployed position at the surgical site. The surgical guide may include a shield configured to bound a work area in the deployed position and a housing including first and second housing portions coupled to respective end portions of the shield. The second housing portion may be pivotable relative to an axis of the first housing portion to move the shield between the folded position and the deployed position. The housing may include a resection slot extending from the work area. The method may include positioning a bone in the work area such that the shield at least partially surrounds a periphery of the bone. The method may include inserting a cutting instrument through the resection slot and into the work area to resect the bone.

In a further implementation, the step of positioning the bone in the work area may occur such that the shield and the housing may cooperate to substantially surround the periphery of the bone.

In a further implementation, the surgical guide may include a handle releasably secured to the first housing portion along an interface. An entrance to the resection slot may be established along the interface. The method may include moving an actuation member to unlock the handle from the second housing portion, and then moving the handle along the interface to detach the handle from the housing. The step of inserting the cutting instrument may include moving the cutting instrument through the entrance of the resection slot subsequent to detaching the handle.

In a further implementation, the method may include inserting an alignment rod into an aperture of the handle. The method may include moving the surgical guide along the periphery of the bone to adjust an angle between the alignment rod and an axis of the bone, and then inserting one or more fastening elements through the housing and then into the bone to secure the surgical guide.

In a further implementation, the resection slot may be established along the axis.

In a further implementation, the method may include moving the surgical guide in the folded position through a soft tissue passage prior to positioning the bone in the work area.

In a further implementation, the bone may be a humeral head of a humerus.

FIG. 1 illustrates a surgical guide 20 for positioning a surgical instrument. The surgical guide 20 may be utilized for various surgical procedures, including preparation of a surgical site during an orthopedic procedure. The surgical guide 20 may be utilized to orient a cutting instrument to resect, cut or otherwise remove a portion of bone. The surgical guide 20 may be utilized to protect tissue adjacent to the bone during the resection and may be utilized to retract or otherwise move the bone to a specified position.

The surgical guide 20 can include a shield 22 coupled to a housing 24. The shield 22 can be dimensioned to capture a portion of bone during an orthopedic procedure, such as during resection of the bone. The shield 22 can include a first shield portion 30 and a second shield portion 30 coupled to the housing 24. The surgical guide 20 can include a handle 26 for manipulation by a surgeon or another user to position the guide 20 during a procedure. The handle 26 may provide opening leverage and reach when manipulating the guide 20.

Figure 2:
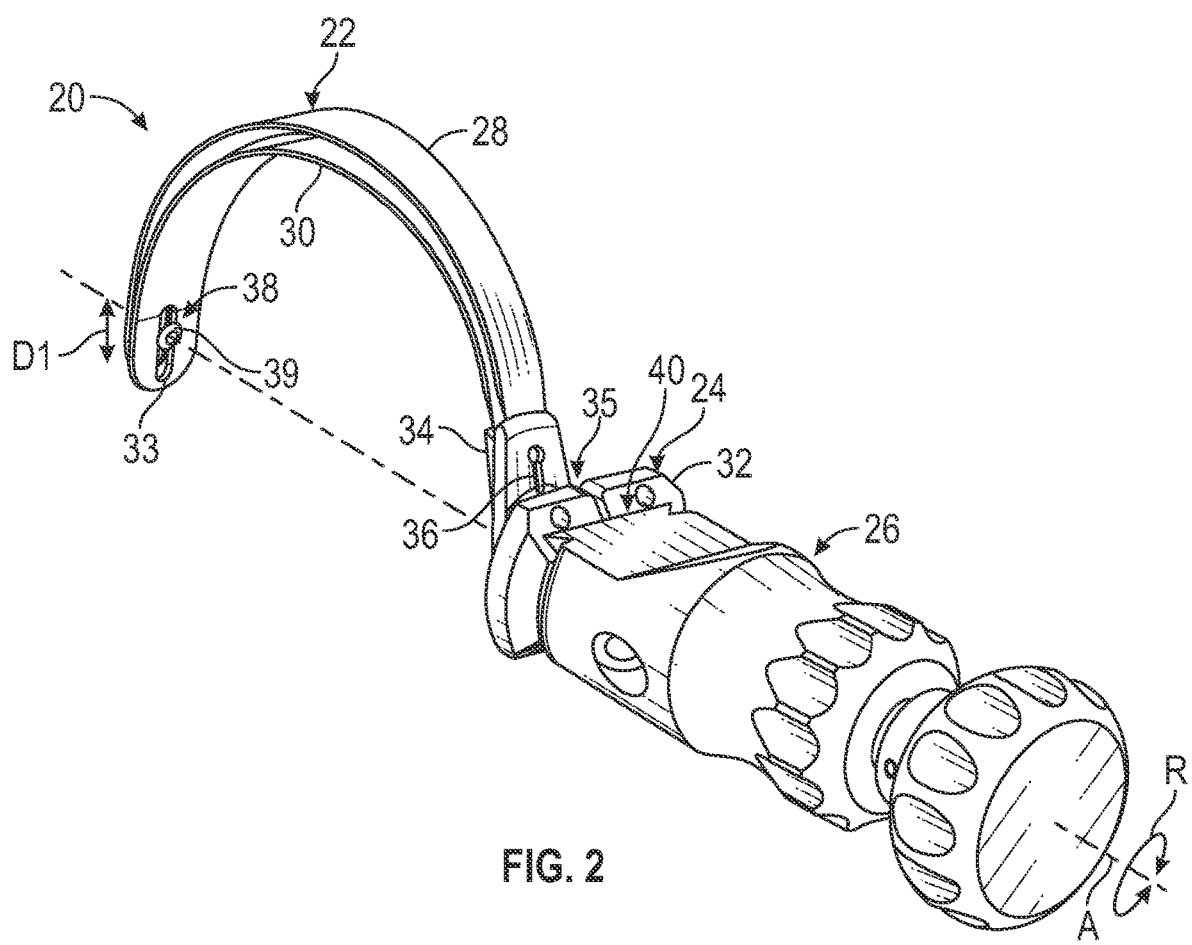
FIG. 2 illustrates the surgical guide of FIG. 1 in a folded position.

Referring to FIGS. 1 and 2, the housing 24 can include a first housing portion 32 and a second housing portion 34 coupled to each other. The first and second housing portions 32, 34 can be coupled to respective end portions of the shield 22. The first shield portion 28 can be coupled to the first housing portion 32. The second shield portion 30 can be coupled to the second housing portion 34. The first and second housing portions 32, 34 can be moveable relative to each other to facilitate insertion and placement of the shield 22 at a surgical site. The first housing portion 32 and second housing portion 34 can be pivotably coupled to each other to establish a deployed (e.g., first or unfolded) position and a folded (e.g., second) position, as illustrated in FIGS. 1 and 2, respectively. The guide 20 can be relatively more compact in the folded position than in the deployed position, which can serve to reduce a size of an incision or passage through the adjacent soft tissue for accessing a bone.

The first and second shield portions 28, 30 of the shield 22 can be movable relative to each other between the folded position and the deployed position in response to relative rotation between the first housing portion 32 and the second housing portion 34 in a rotational direction R about an axis A (FIG. 2). The axis A can be a longitudinal axis extending through the housing 24 of the surgical guide 20. The first and second housing portions 32, 34 can be pivotable relative to each other about the axis A to move the shield 22 between the folded position and the deployed position.

Figure 6A:
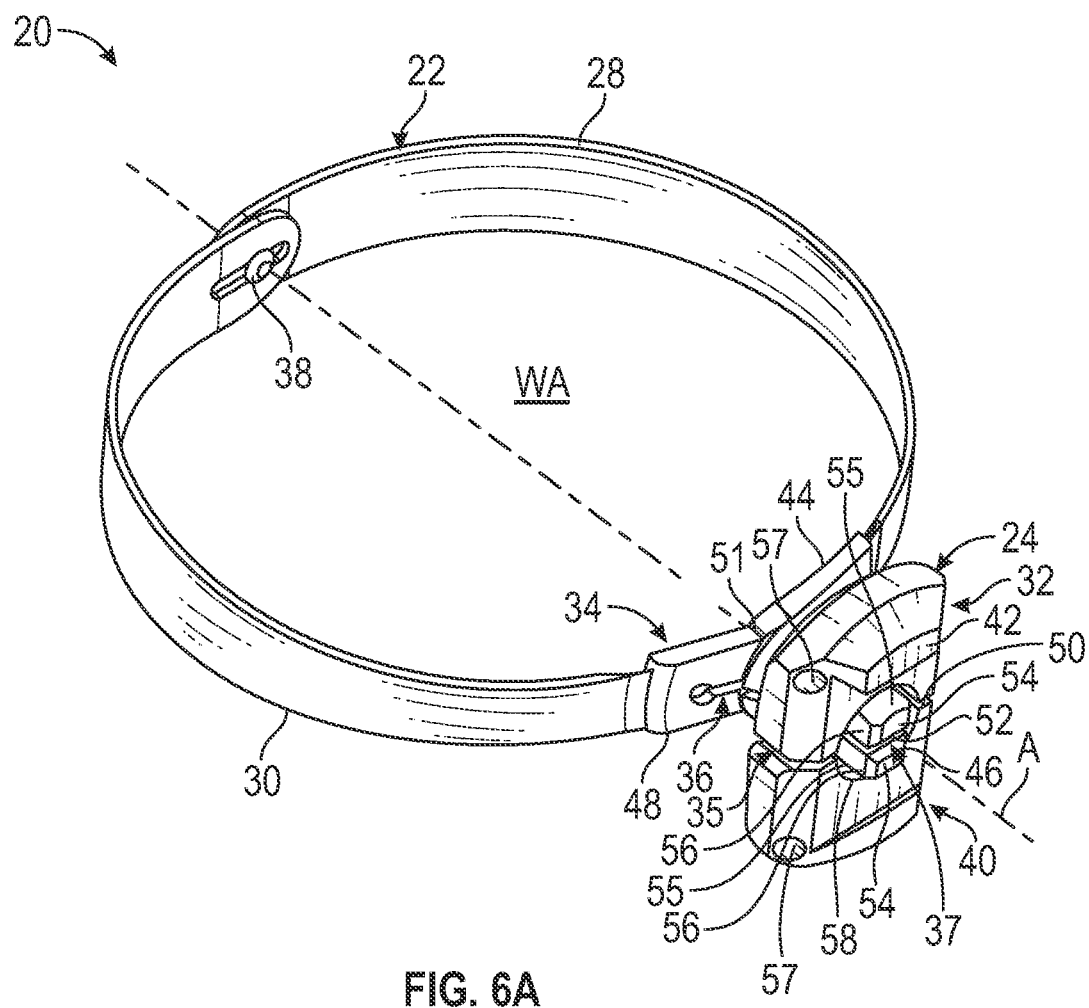
FIG. 6A illustrates the surgical guide of FIG. 1 in the deployed position with a handle removed.

The first and second shield portions 28, 30 of the shield 22 can be configured to bound a work area WA in the deployed position (see, e.g., FIG. 1). The work area WA can be dimensioned to receive a portion of bone. The bone may be resected or otherwise cut by a cutting instrument positioned by the surgical guide 20, including any of the cutting instruments disclosed herein. The shield portions 28, 30 can be dimensioned to at least partially surround a perimeter of the work area WA in the deployed position. The shield 22 can have a substantially hoop-shaped geometry. The first shield portion 28 and/or second shield portion 30 can have a generally arcuate geometry. In implementations, the first and second shield portions 28, 30 of the shield 22 can have a generally semi-circular geometry. The first and second shield portions 28, 30 of the shield 22 can be dimensioned to cooperate with the housing 24 to encircle the work area WA in the deployed position, as illustrated in FIGS. 1 and 6A.

The surgical guide 20 may be made of various materials, including metallic and/or non-metallic materials such as a surgical grade steel or bio-compatible polymer. The first and second shield portions 28, 30 of the shield 22 can be flexible such that the portions 28, 30 are substantially conformable to a periphery of a portion of bone captured in the work area WA.

Distal ends of the first and second shield portions 28, 30 can be pivotably coupled to each other at a connection 38. The connection 38 can be spaced apart from the housing 24. The connection 38 can serve as a pivot point of the shield 22. The axis A can be dimensioned to extend through the distal ends of the first and second shield portions 28, 30 at the connection 38 such that the pivot point is established along the axis A.

Various techniques can be utilized to establish the connection 38. In implementations, the connection 38 can be established by a fastening element 39 at least partially received in a pair openings 31, 33 in the respective shield portions 28, 30 to mechanically attach the shield portions 28, 30 to each other (see, e.g., FIGS. 2-3; the fastening element 39 is omitted from FIG. 3 for illustrative purposes). The fastening element 39 can be a rivet or a threaded bolt and nut, for example.

The connection 38 can be adjusted to accommodate different bone sizes and geometries. The openings 31, 33 can be elongated slots at least partially aligned to receive the fastening element 39. The fastening element 39 can be moved in a direction D1 (FIG. 2) relative to the openings 31, 33 to increase, decrease or otherwise vary the perimeter or size of the work area WA. The direction D1 can be substantially perpendicular or otherwise transverse to the axis A. For the purposes of this disclosure, the term "substantially"

means within 90% of the stated value or relationship unless otherwise indicated. In other implementations, the connection 38 can be omitted, and the first and second shield portions 28, 30 can be a pair of arcuate arms with the distal ends spaced apart from each other in the deployed position.

The surgical guide 20 can include at least one guide passage 35 dimensioned to position and orient a cutting instrument or another surgical instrument along a determined trajectory. Each guide passage 35 can have various geometries, such as a generally elliptical cross-sectional geometry dimensioned to receive a drill or a generally rectangular cross-sectional geometry dimensioned to receive a milling tool. In implementations, the guide 20 can be a resection guide, and the guide passage 35 can be a resection slot 36. The cutting instrument can be a bone saw having cutting teeth configured to resect or otherwise cut a portion of bone captured in the work area WA. The resection slot 36 can be dimensioned to extend along a reference (e.g., resection) plane REF1 (see, e.g., FIGS. 8-9). The resection slot 36 can be dimensioned to extend outwardly from the work area WA, and a projection of the reference plane REF1 can be dimensioned to intersect the work area WA (see also FIG. 9). The resection plane REF1 can extend along or can otherwise be substantially parallel to the axis A. In other implementations, the resection plane REF1 can be transverse to the axis A. The resection slot 36 can be dimensioned to receive a surgical instrument such as a cutting instrument. The resection slot 36 can be dimensioned to receive a selected cutting instrument along the reference plane REF1.

Guide passages 35 can be established various positions along the guide 20. The housing 24 can establish at least one guide passage 35, such as the resection slot 36. Guide passages 35 can be established at other positions along the guide 20. In implementations, the shield 22 can establish one or more guide passages 35' such as resection slots 36' in the first and/or second shield portions 28, 30 (shown in dashed lines in FIG. 3 for illustrative purposes).

The handle 26 can be releasably secured to the housing 24 along an interface 40. In other implementations, the handle 26 is integrally formed with a portion of the housing 24, such as the first housing portion 32. The surgeon or assistant may attach the handle 26 to the housing 24 prior or subsequent to moving the shield 22 and housing 24 through an incision in the patient and positioning a portion of bone in the work area WA of the shield 22. Detaching the handle 26 from the housing 24 can serve to reduce a size of the guide 20 during placement and prior to deployment.

Figure 3:
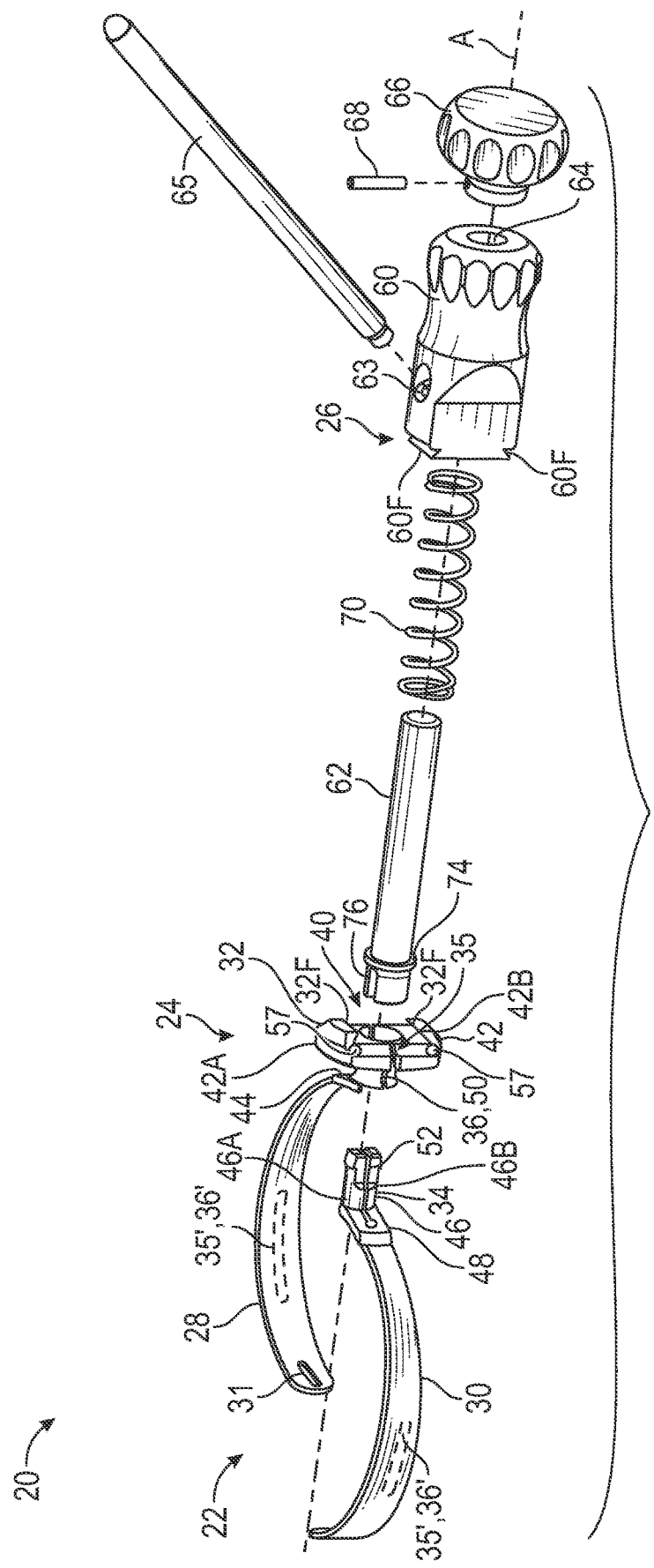
FIG. 3 illustrates an exploded, perspective view of the surgical guide of FIG. 1.

Referring to FIG. 3, with continuing reference to FIGS. 1 and 2, the first housing portion 32 of the housing 24 can include a first body 42 and a first flange 44 extending outwardly from the first body 42. The second housing portion 34 can include a second body 46 and a second flange 48 extending outwardly from the second body 46. The first flange 44 can be coupled to a proximal end of the first shield portion 28 of the shield 22. The second flange 48 can be coupled to a proximal end of the second shield portion 30 of the shield 22. The first flange 44 and/or second flange 48 can have a generally arcuate geometry dimensioned to follow a curvature of the respective shield portions 28, 30.

The resection slot 36 can be established by various portions of the housing 24. In implementations, the surgical guide 20 can include a first slot 50 extending through the first housing portion 32 and a second slot 52 extending through the second housing portion 34. The first slot 50 can be dimensioned to divide the first body 42 into opposed body portions 42A, 42B (see also FIG. 9). The body portions 42A, 42B can be connected by the first flange 44. The body portions 42A, 42B can be substantially symmetric or can differ in geometry. The second slot 52 can be dimensioned to divide the second body 46 into opposed body portions 46A, 46B (see also FIG. 9). The body portions 46A, 46B can be connected by the second flange 48. The body portions 46A, 46B can be substantially symmetric or can differ in geometry.

Figure 6B:
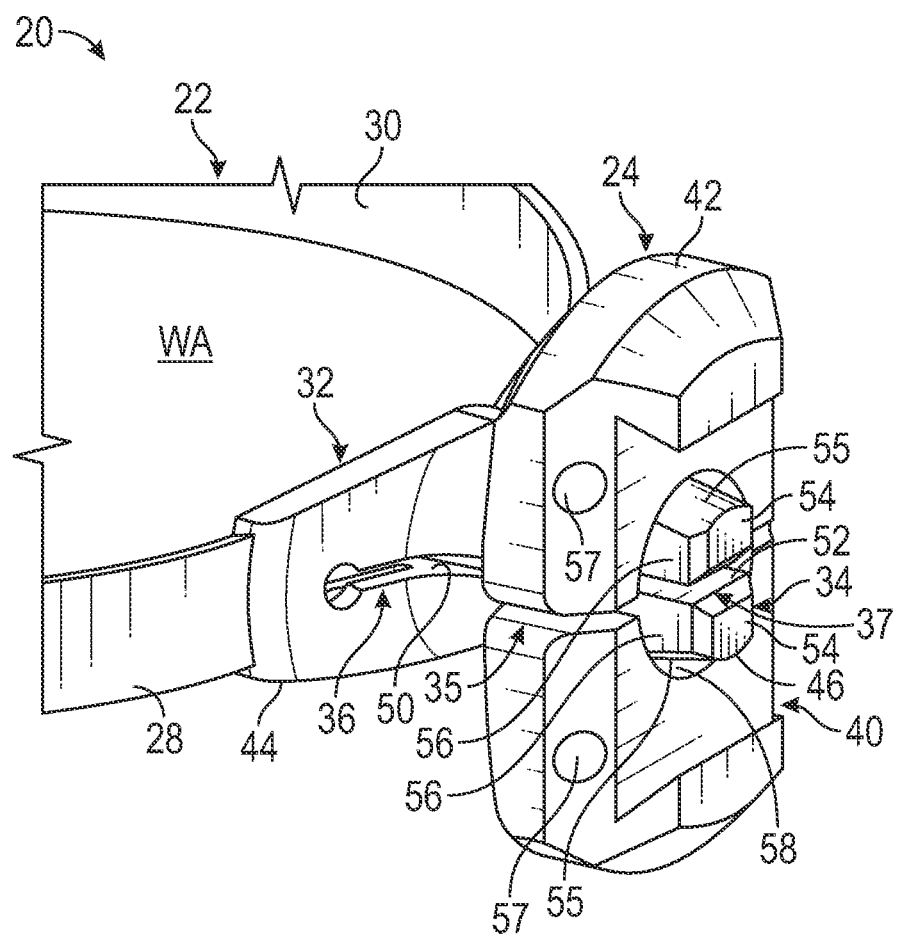
FIG. 6B illustrates portions of the surgical guide of FIG. 6A.
Figure 7:
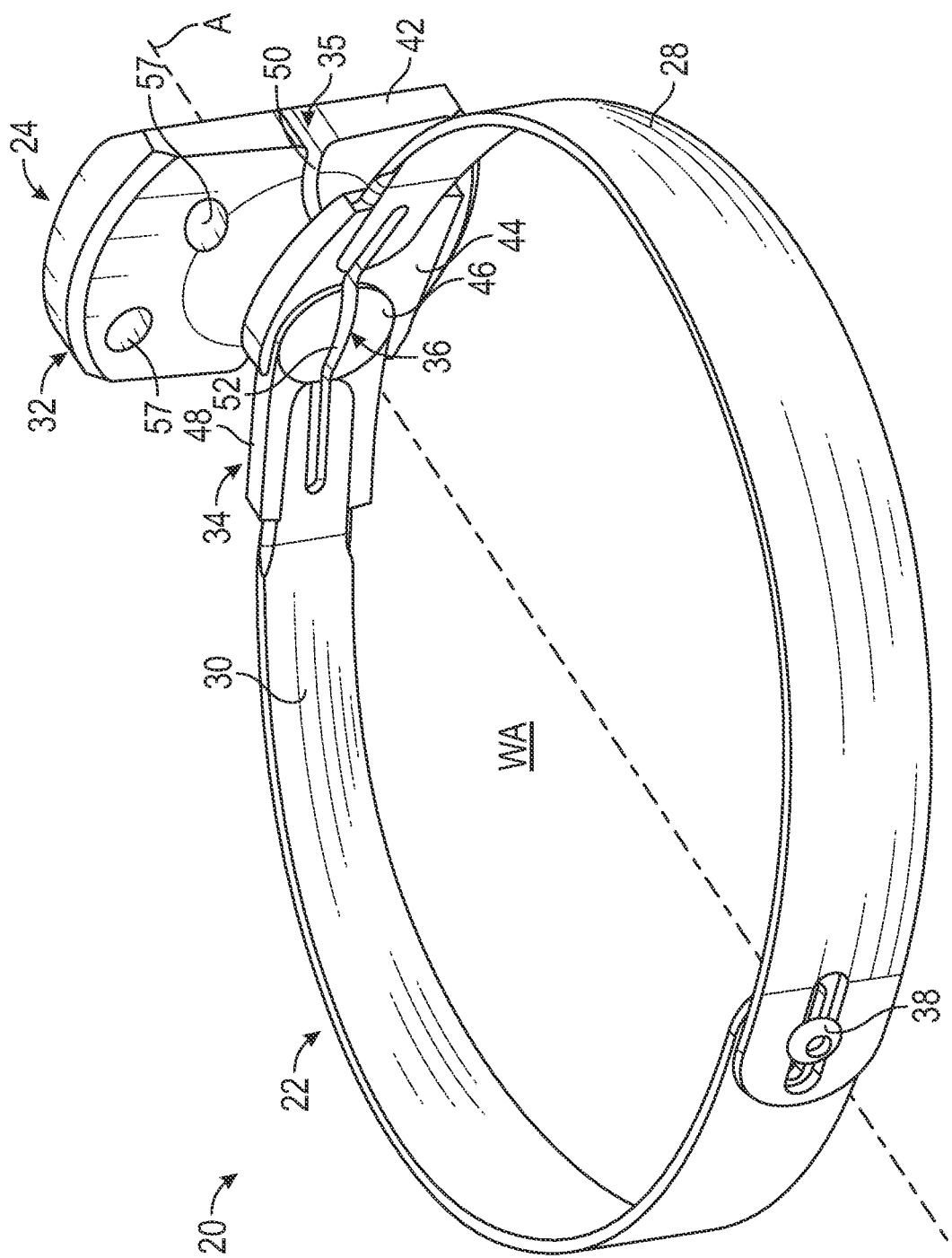
FIG. 7 illustrates another perspective view of the surgical guide in the deployed position with the handle removed.
Figure 8:
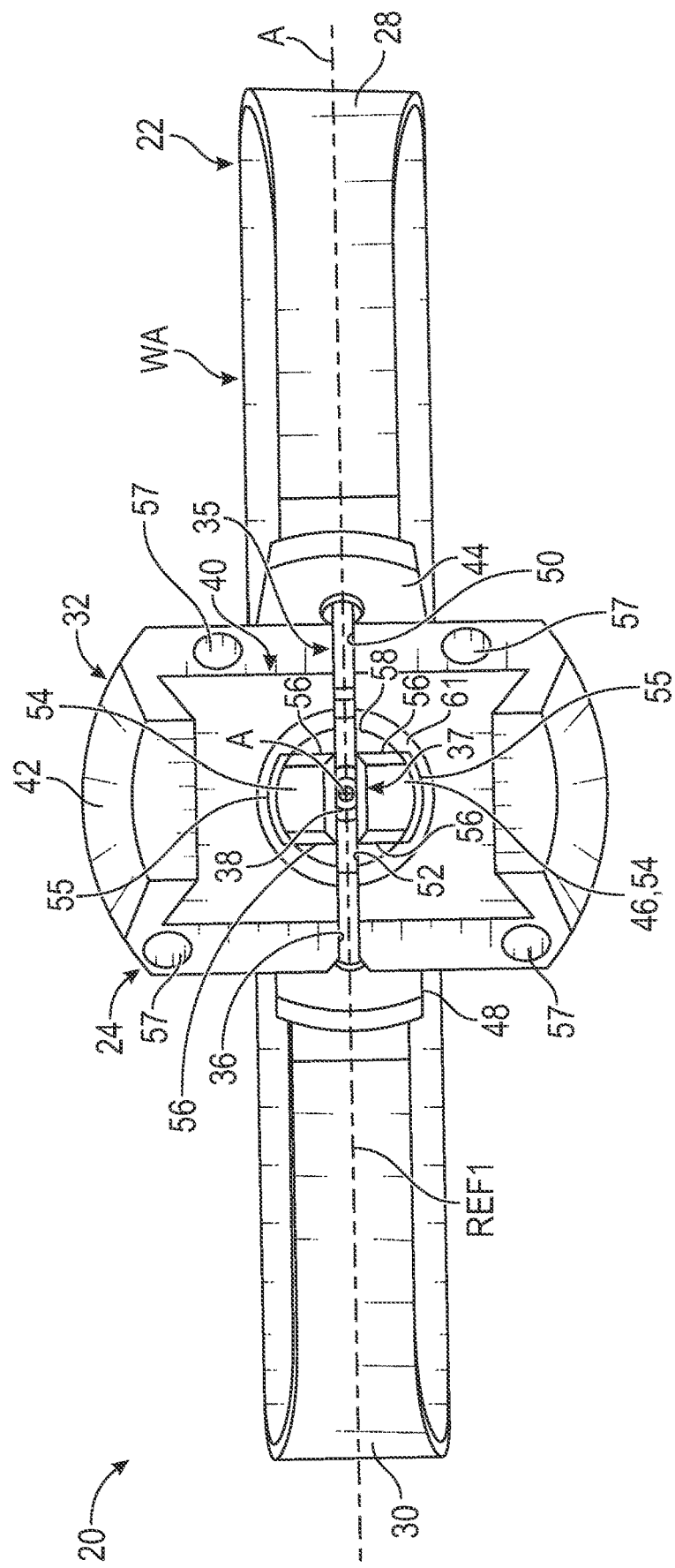
FIG. 8 illustrates an axial view of the surgical guide of FIG. 7.
Figure 9:
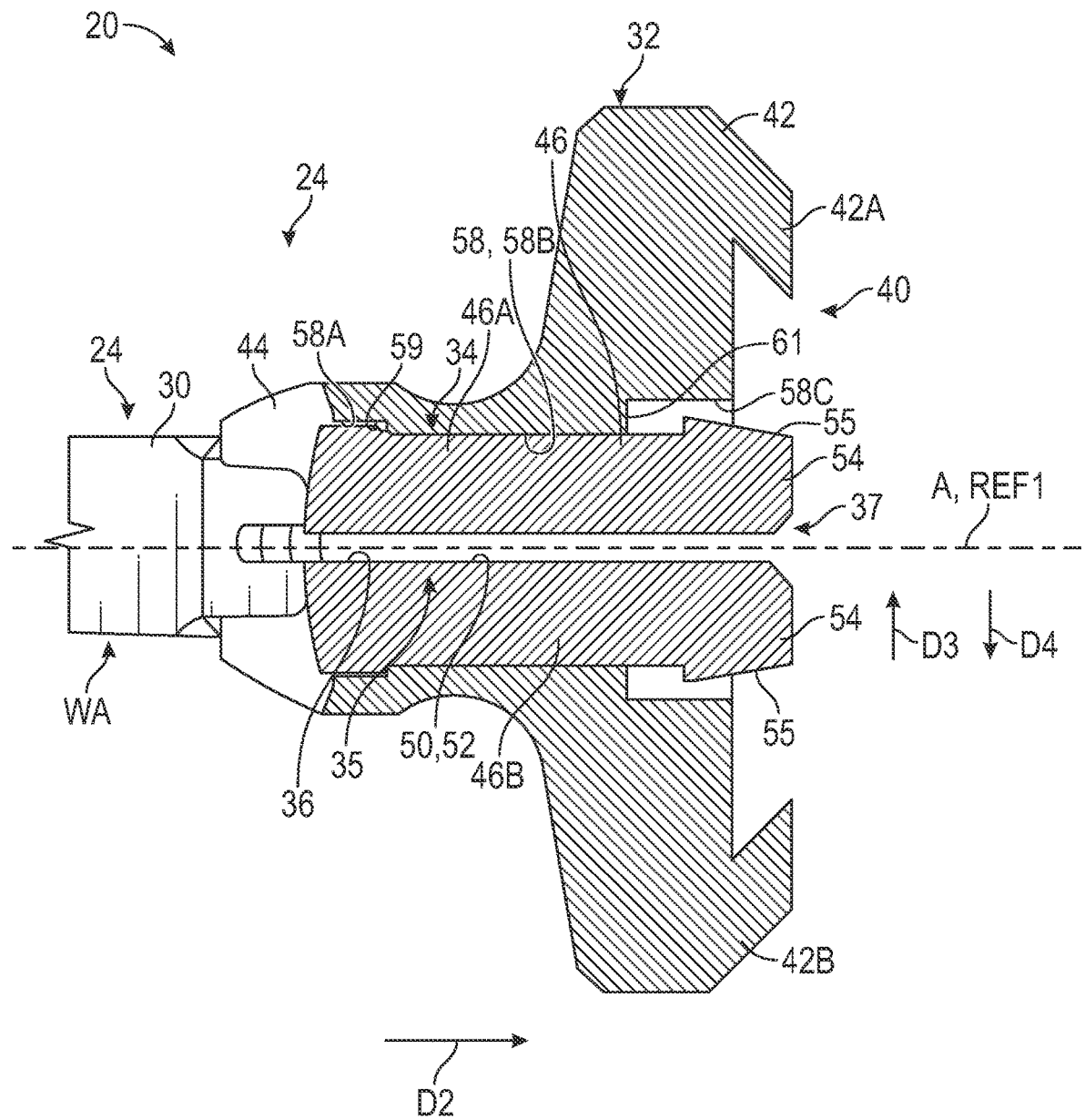
FIG. 9 illustrates a sectional view of the surgical guide of FIG. 6B with the handle removed.

The first and second slots 50, 52 can be substantially aligned along the reference plane REF1 in the deployed position to establish the resection slot 36, as illustrated in FIGS. 8-9 (see also FIGS. 6A-6B). Opposed walls of the flanges 44, 48 can bound a width of the resection slot 36 in the deployed position. The resection slot 36 can be established along the axis A, as illustrated in FIG. 8. The resection slot 36 can extend between the interface 40 and the work area WA, as illustrated in FIGS. 6A-6B and 9. The first slot 50 and second slot 52 can be transverse to each other in response to relative rotation in the direction R or otherwise moving the shield 22 between the deployed position and the folded position, as illustrated in FIG. 10.

Figure 10:
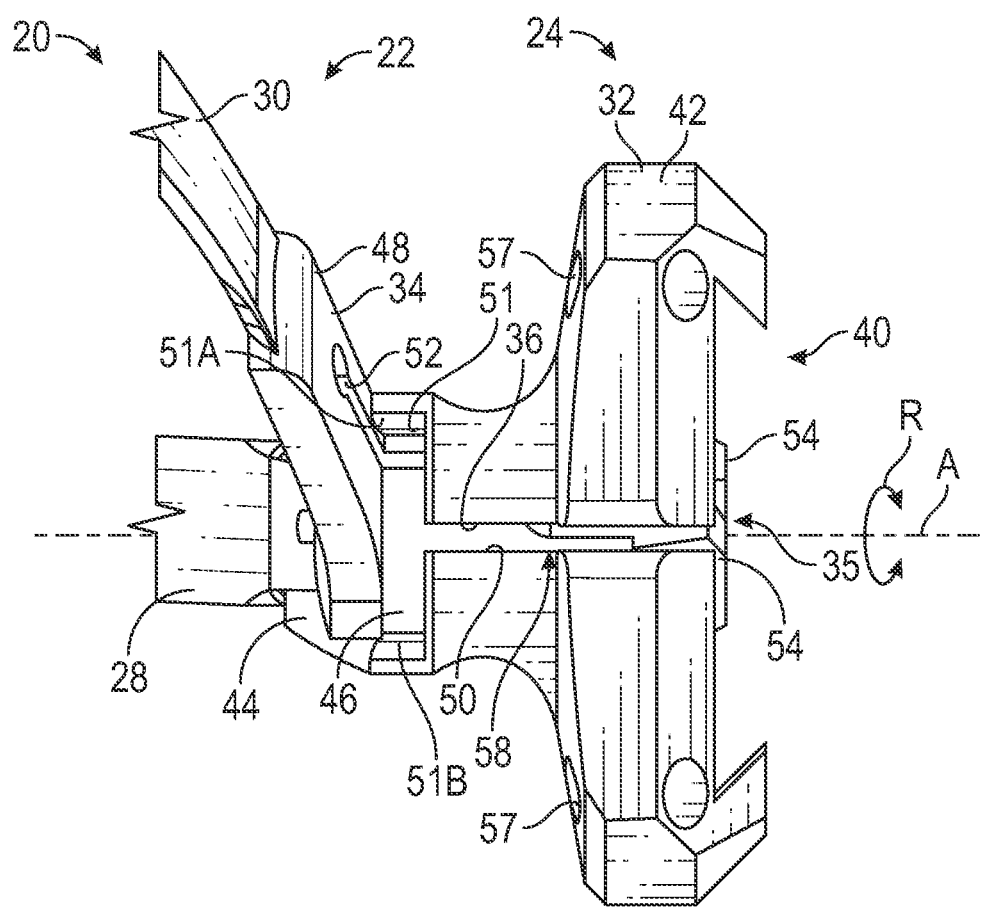
FIG. 10 illustrates another side view of portions of the surgical guide between the folded position and the deployed position with the handle removed.

The first housing portion 32 can include a channel 51 extending outwardly from the passageway 58, as illustrated in FIG. 10. The channel 51 can be dimensioned to at least partially receive the second flange 48 in response to rotating the second housing portion 34 about the axis A and then translating the second body 46 along the axis A towards a proximal end of the first body 42. The second flange 48 can be dimensioned to abut against opposed walls 51A, 51B of the channel 51 to limit relative rotation between the first and second housing portions 32, 34 about the axis A in the deployed position. The first body 42 can be concentric with the second body 46 along the axis A.

The housing 24 can include one or more apertures 57. Each aperture 57 can be dimensioned to at least partially receive a respective fastening element 78 to secure the surgical guide 20 to bone (see, e.g., FIGS. 17-18). The fastening elements 78 can be pins, wires or screws, for example. The apertures 57 can be established in the first housing portion 32 or another portion of the housing 24.

Figure 4:
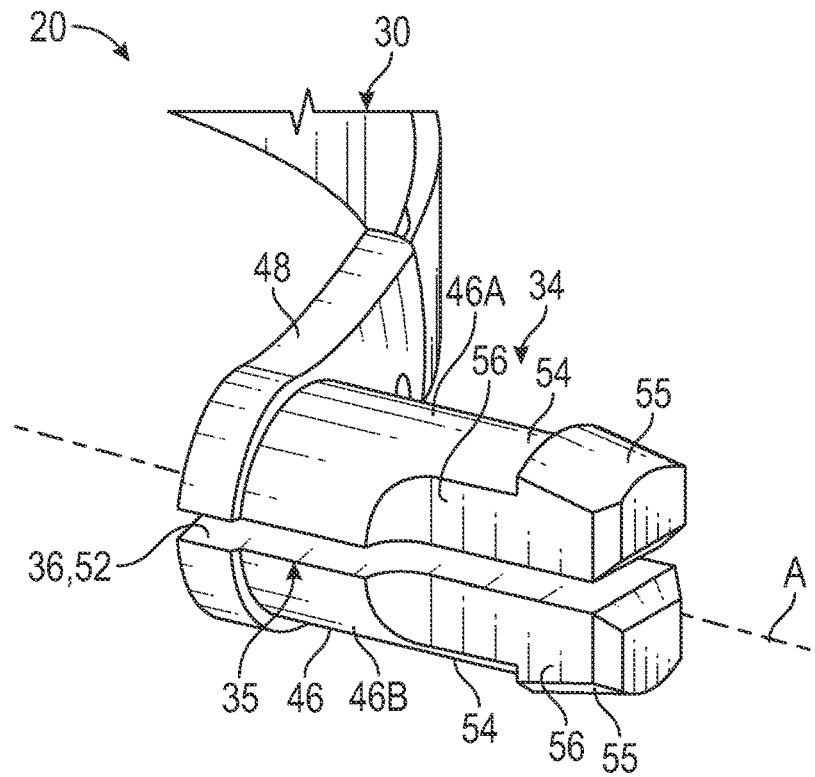
FIG. 4 illustrates a perspective view of a second housing portion of the surgical guide.
Figure 5:
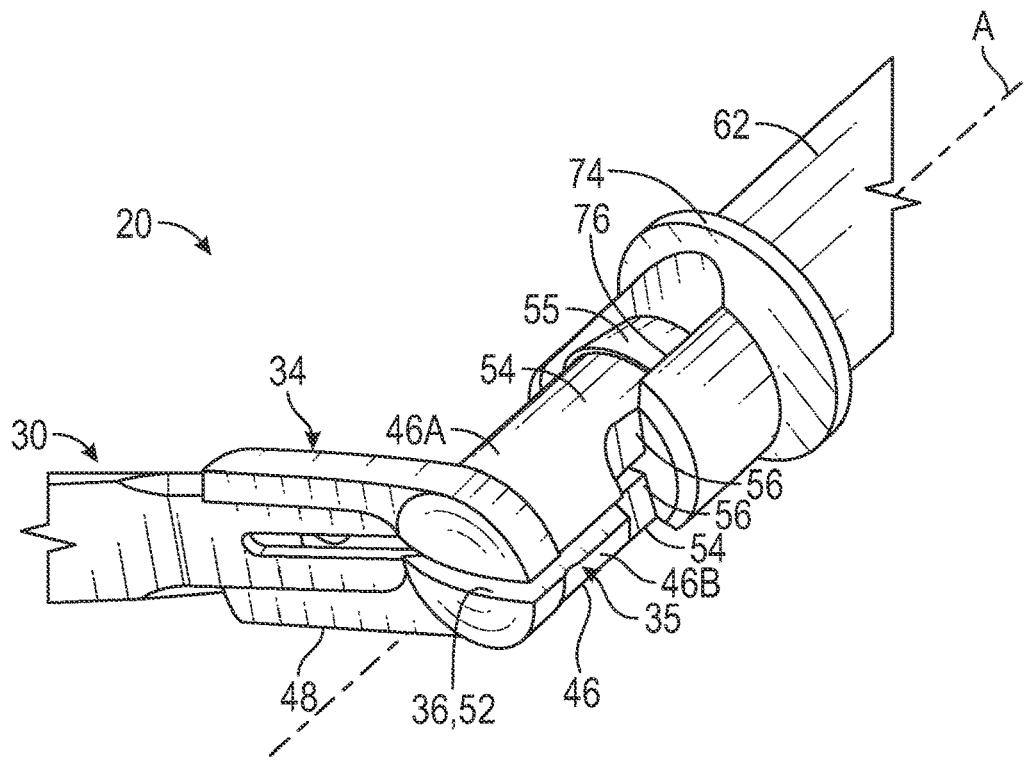
FIG. 5 illustrates a perspective view of the second housing portion of FIG. 4 engaged with an actuation member.

Various techniques can be utilized to secure the first housing portion 32 and the second housing portion 34 to each other. Referring to FIGS. 4-5 and 8, with continuing reference to FIG. 3, the second housing portion 34 can include a pair of lock members 54 that establish the body portions 46A, 46B of the second body 46. The lock members 54 can face each other along opposite sides of the resection slot 36. Each of the lock members 54 can include a protrusion 55 between a pair of flats 56. The flats 56 can be established on opposite sides of the respective lock member 54.

Referring to FIG. 9, with continuing reference to FIGS. 4-5, the first body 42 of the first housing portion 32 can include an elongated passageway 58. The passageway 58 can extend along the axis A and/or resection slot 36. The passageway 58 can include first, second and third regions 58A, 58B, 58C. The second region 58B can be dimensioned to interconnect, and can have a lesser diameter than, the first and third regions 58A, 58C. The first region 58A can extend distally along the axis A to a first shoulder 59. The third region 58C can extend proximally along the axis A to a second shoulder 61. The first and second shoulders 59, 61 can be established on opposite sides of the second region 58B.

The lock members 54 can be insertable in a second direction D2 into and at least partially through the passageway 58. The second direction D2 can be substantially parallel to the axis A. A width across the protrusions 55 can be greater than a diameter of the second region 58B. The lock members 54 can be configured to deflect inwardly in a third direction D3 in response to being inserted in the first region 58A of the passageway 58 and contacting the first shoulder 59. The lock members 54 can be configured to then deflect outwardly in a fourth direction D4 in response to exiting proximally from the second region 58B and being inserted in the third region 58C of the passageway 58 to lock the second body 46 at least partially in, or otherwise to, the first body 42. The fourth direction D4 can be generally opposed to the third direction D3. The third direction D3 can extend towards the axis A. The fourth direction D4 can extend away from the axis A. The protrusions 55 can be dimensioned to abut against the second shoulder 61 along the third region 58C of the passageway 58 to inhibit removal of the second body 46 from the passageway 58.

Referring to FIG. 11A, with continuing reference to FIG. 3, the handle 26 can include an elongated main body 60 dimensioned to extend along the axis A. The main body 60 can be contoured to facilitate manipulation by the surgeon. The main body 60 can include one or more apertures 63. The apertures 63 can be distributed about a periphery of the main body 60. Each of the apertures 63 can be dimensioned to receive a respective alignment rod 65 (FIG. 3). The alignment rod 65 can be threaded in the aperture 63 to mechanically attach or otherwise secure the alignment rod 65 to the housing 24. The alignment rod 65 can be utilized to orient the guide 20 relative to a bone captured by the guide 20 and/or another portion of the anatomy.

Various techniques can be utilized to releasably secure the handle 26 to the housing 24. In implementations, the main body 60 and the first housing portion 32 can be releasably secured or otherwise coupled to each other along the interface 40 with mating flanges 32F, 60F. The flanges 32F, 60F can cooperate to establish a dovetail connection along the interface 40.

The guide 20 can include a lock mechanism to releasable secure the housing 24 and handle 26 to each other. In implementations, the lock mechanism is established by an actuation member 62. The actuation member 62 can be captured in the main body 60 of the handle 26. The actuation member 62 can include an elongated shaft at least partially received in a passageway 64 established in the main body 60. The passageway 64 can include a first region 64A and a second region 64B extending from the first region 64A. The first region 64A can have a diameter that is greater than a diameter of the second region 64B to establish a shoulder 72.

The handle 26 can include a control knob 66 secured to an end portion of the actuation member 62. The control knob 66 can be secured to the actuation member 62 with a fastener 68 such as a pin or threaded bolt. The surgeon or assistant can manipulate the control knob 66 to move the actuation member 62 along the axis A between a first (e.g., locked) position and a second (e.g., unlocked) position relative to the interface 40, as illustrated by FIGS. 11A and 11B, respectively.

The handle 26 can include a spring member 70. The spring member 70 can be a coil spring carried by a periphery of the actuation member 62. The spring member 70 can be received in the first region 64A of the passageway 64. The spring member 70 can be trapped between the shoulder 72 and an annular flange 74 of the actuation member 62. The spring member 70 can be dimensioned to bias the actuation member 62 in a fifth direction D5 towards the housing 24.

The actuation member 62 can include a recess 76 established along a distal end of the actuation member 62. The recess 76 can be dimensioned to at least partially receive a proximal end of the second body 46 of the second housing portion 34 in the locked position (see also FIG. 5). Walls of the recess 76 of the actuation member 62 can be configured to engage the flats 56 of the lock members 54 of the second housing portion 34 in the locked position to lock the handle 26 to the housing 24, as illustrated in FIG. 11A. The actuation member 62 can be configured to disengage the lock members 54 in the unlocked position such that the handle 26 is releasable from the housing 24, as illustrated in FIG. 11B.

The distal end of the handle 26 can be releasably secured to the first housing portion 32 along the interface 40. The actuation member 62 can be moveable in the fifth direction D5 towards the second housing portion 34 to engage the lock members 54 in the locked position, as illustrated in FIG. 11A. The actuation member 62 can be moveable in a sixth direction D6 away from the second housing portion 34 to disengage the lock members 54 in the unlocked position, as illustrated in FIG. 11B. The direction D5 may be a distal direction, and the direction D6 may be a proximal direction relative to the guide 20. The directions D5, D6 can be generally opposed to each other relative to the axis A. The directions D5, D6 can be generally parallel to the axis A. Moving the actuation member 62 in the sixth direction D6 can cause the spring member 70 to compress. The spring member 70 can bias the actuation member 62 in the fifth direction D5, which can cause the spring member 70 to decompress.

The actuation member 62 can be configured to engage the lock members 54 of the second housing portion 34 in the locked position to lock the handle 26 to the housing 24. Locking the handle 26 to the housing 24 can occur to block access to an entrance 37 of the resection slot 36 (see also FIGS. 6A-6B and 8-9). The entrance 37 can be established along the interface 40 or another portion of the housing 24 and/or shield 22. The actuation member 62 can be configured to extend across the interface 40 in the locked position to limit separation between the handle 26 and the housing 24.

The actuation member 62 can be configured to disengage the lock members 54 of the second housing portion 34 in the unlocked position (FIG. 11B) such that the handle 26 is releasable from the first housing portion 32 to provide access to the entrance 37 of the resection slot 36. The handle 26 can be moved along the interface 40 in a direction perpendicular or otherwise transverse to the axis A to disengage the handle 26 from the housing 24. In implementations, the handle 26 can be moved in a direction along the interface 40 that is substantially parallel to the reference plane REF1 of the resection slot 36 to attach and detach the handle 26 (see FIG. 8).

Figure 12:
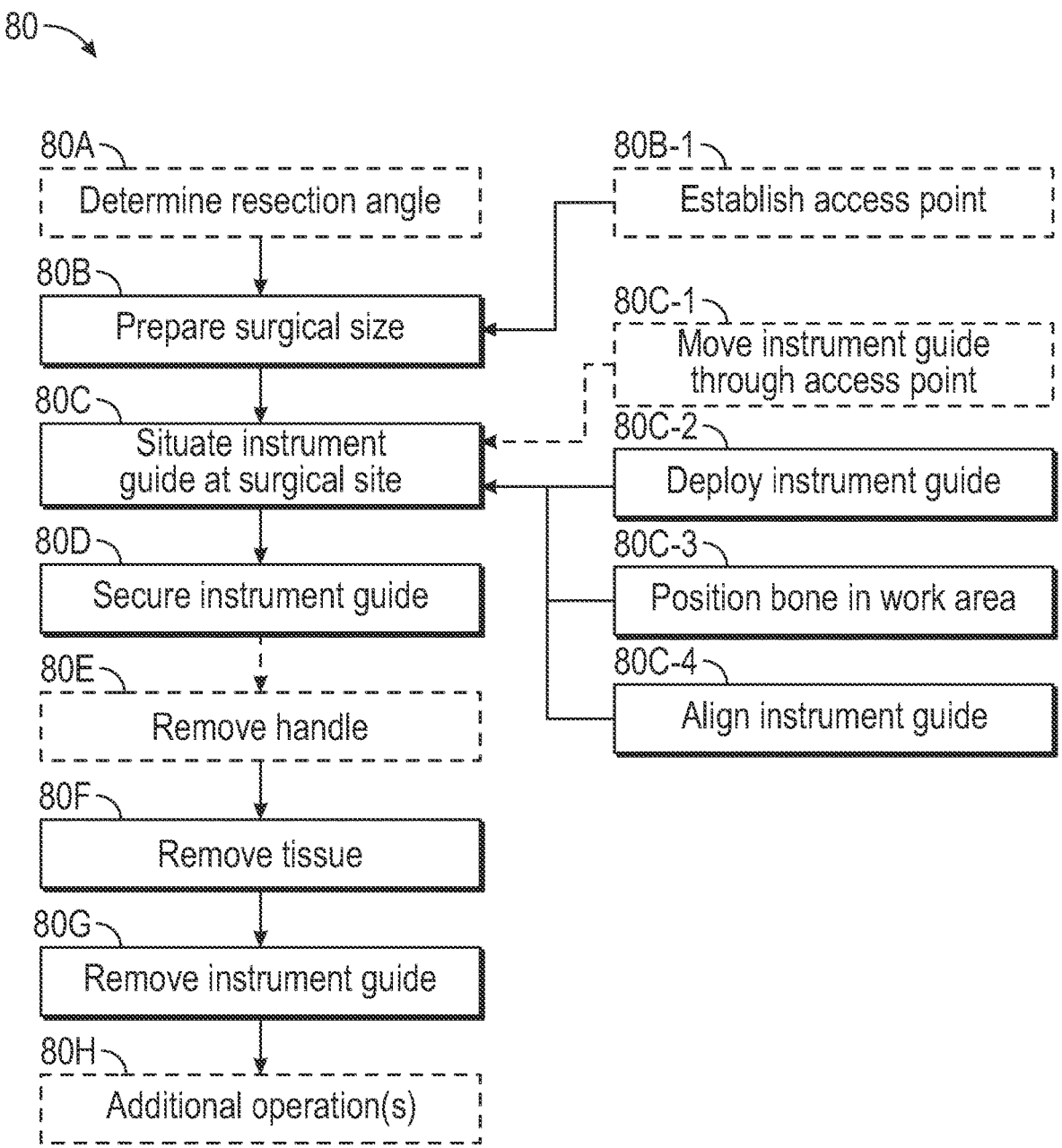
FIG. 12 illustrates an exemplary method of performing a surgical procedure.

FIG. 12 illustrates an exemplary method of performing a surgical procedure in a flowchart 80. The method 80 may be utilized to perform various orthopaedic procedures, such as an arthroplasty for restoring functionality to shoulders and other joints such as hips, knees, elbows, wrists, etc. The method 80 can include removing a portion of bone or other tissue in preparation for placement of an orthopaedic implant or graft. Although the method 80 primarily refers to resection of an articular surface of a humeral head of a humerus during a shoulder reconstruction, it should be understood that the method may be utilized in other anatomical locations of a patient, such as articular and/or non-articular surfaces of a bone. The method 80 may be utilized to implement other surgical procedures, including drilling, milling and burring operations to remove tissue such as bone. The method 80 can be utilized with any of the guides disclosed herein, including the surgical guide 20. Fewer or additional steps than are recited below could be performed within the scope of this disclosure, and the recited order of steps is not intended to limit this disclosure.

Figure 13:
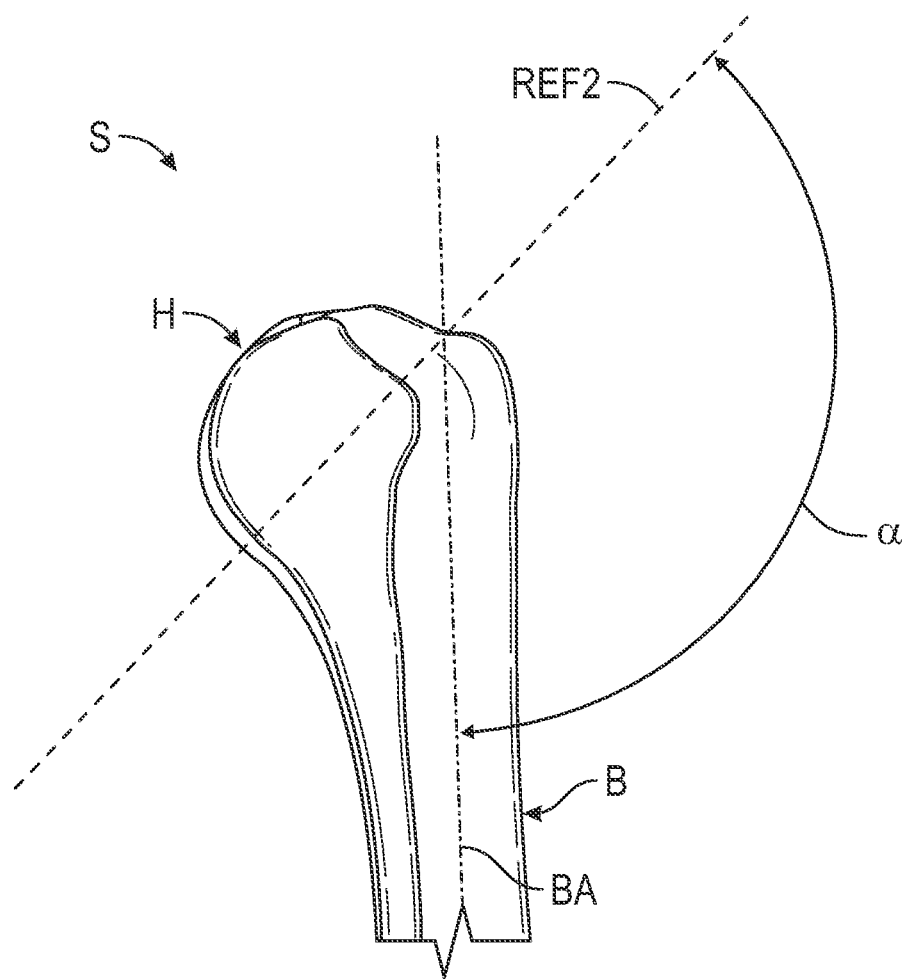
FIG. 13 illustrates an exemplary resection angle relative to a bone.

Referring to FIG. 13, with continuing reference to FIG. 12, a resection angle α may be determined at step 80A. The resection angle α may be established between an axis BA of a bone B and a reference plane REF2 for a surgical site S. The reference plane REF2 may intersect a portion of the bone B. The reference plane REF2 and associated resection angle α may be determined preoperatively and/or intra-operatively. The bone B may be a long bone or another bone. The axis BA may be a longitudinal axis extending between opposed end portions of the bone B (see, e.g., FIG. 16). The bone B may include an articular surface establishing a portion of a joint J, such as a shoulder joint (see, e.g., FIGS. 14-15) or another joint of the patient. The portion of bone B may be include an articular surface established by an end portion of a bone, such as a humeral head H of a humerus.

Figure 14:
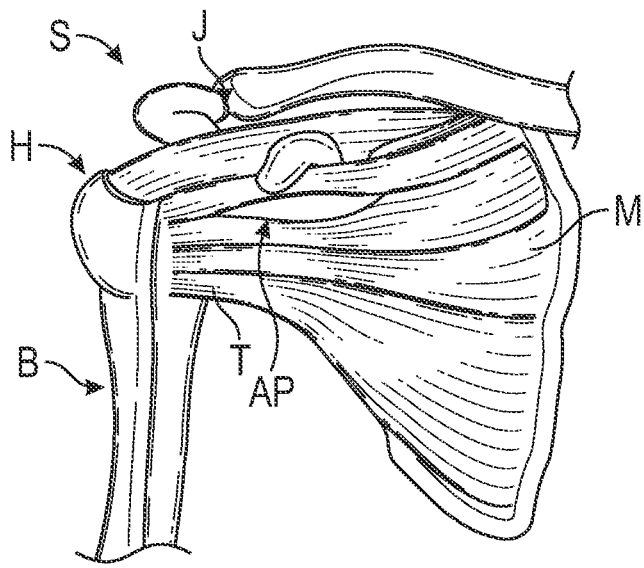
FIG. 14 illustrates an access point relative to the bone of FIG. 13.

Referring to FIG. 14, with continuing reference to FIG. 12, the surgical site S may be prepared at step 80B. Step 80B can include establishing an incision through the skin of a patient. Step 80B can include establishing an access point AP through tissue of the patient at step 80B-1. The access point AP may be a bony passage established in bone(s) (e.g., bone B) or may be a soft tissue passage established in soft tissue such as muscle(s) or tendon(s) to provide access to the selected bone B and/or joint J. In implementations, step 80B-1 includes forming an incision in a muscle M to establish the access point AP for exposure of the bone B or joint J. The surgeon may part or separate the muscle M along the fibers to establish a window such that the fibers are not transected. The access point AP may be a soft tissue passage established through the muscle M in response to parting the fibers. The muscle M may be the subscapularis or another portion of the rotator cuff. In other implementations, the access point AP can be established by separating muscle groups at the rotator cuff interval or can be established by partially or completely transecting the muscle M or tendon T.

Figure 15:
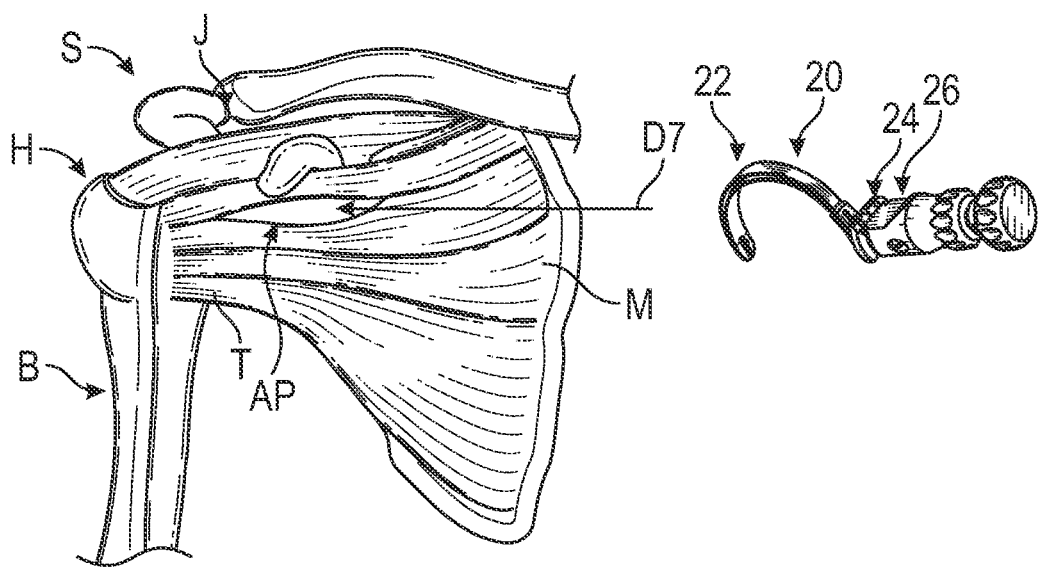
FIG. 15 illustrates a surgical guide positioned relative to the access point of FIG. 14.

Referring to FIG. 15, with continuing reference to FIGS. 12 and 14, at step 80C the surgical guide 20 can be situated at the surgical site S. Step 80C can include moving the surgical guide 20 through the access point AP at step 80C-1. Step 80C-1 can include moving the surgical guide 20 in the folded position through the access point AP, such as a soft tissue passage. Step 80C-1 can include moving the surgical guide 20 in a direction D7 at least partially or completely through the access point AP while in the folded position, including at least the shield 22. Step 80C-1 can include moving the housing 24 at least partially or completely through the access point AP while in the folded or deployed position. Step 80C-1 can occur prior to positioning the bone B in the work area WA. Step 80C can occur such that at least a portion of the handle 26 extends outwardly of the access point AP for manipulation by the surgeon. Moving the surgical guide 20 through the access point AP while in the folded position may reduce a size of the access point AP and any associated incisions, which can promote healing of the patient.

Figure 16:
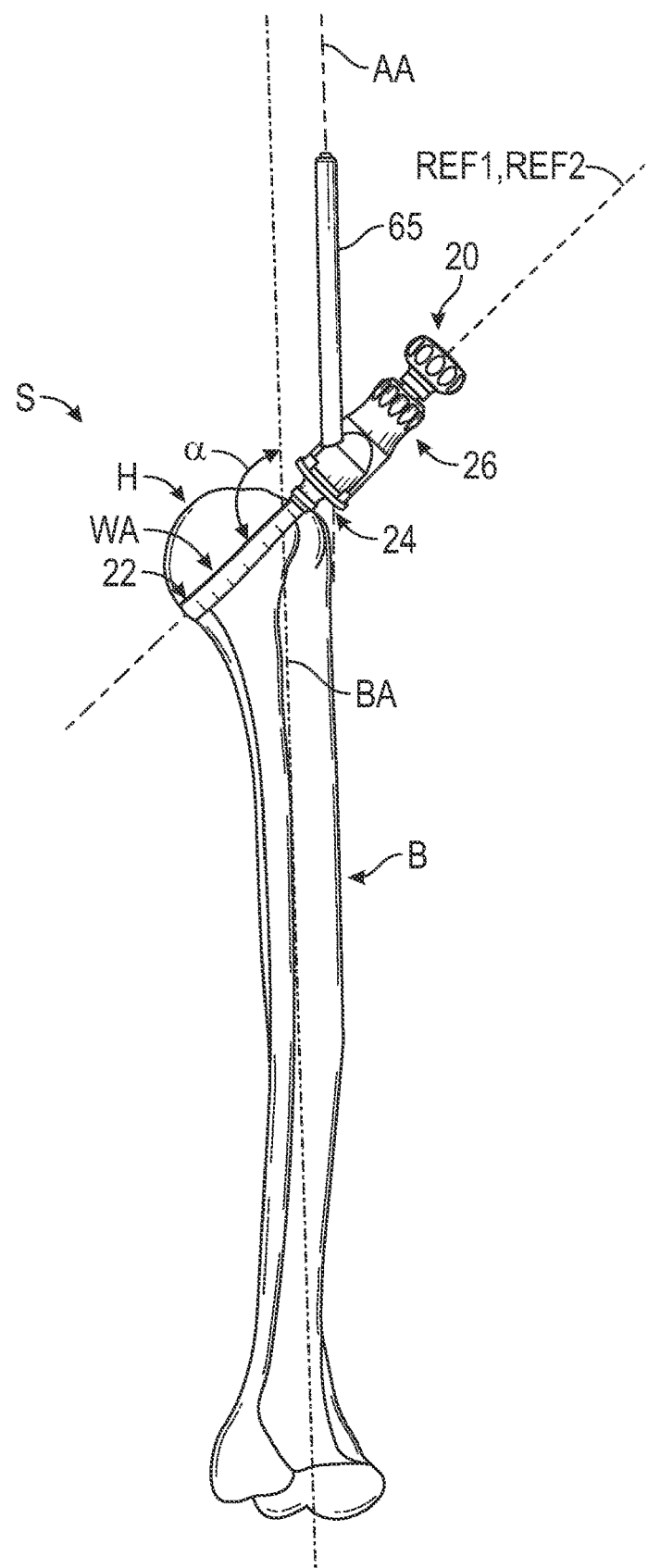
FIG. 16 illustrates the surgical guide and an alignment member positioned relative to the bone of FIG. 15.

Referring to FIG. 16, with continuing reference to FIG. 12, step 80C can include deploying the surgical guide 20 at step 80C-2. Step 80C-2 can include moving the surgical guide 20 between the folded position (e.g., FIG. 15) and the deployed position at the surgical site S. Deploying the surgical guide 20 can occur while the guide 20 is at least partially situated in the patient. Step 80C-2 can occur subsequent to moving the surgical guide 20 including the shield 22 through the access point AP at step 80C-1.

Figure 17:
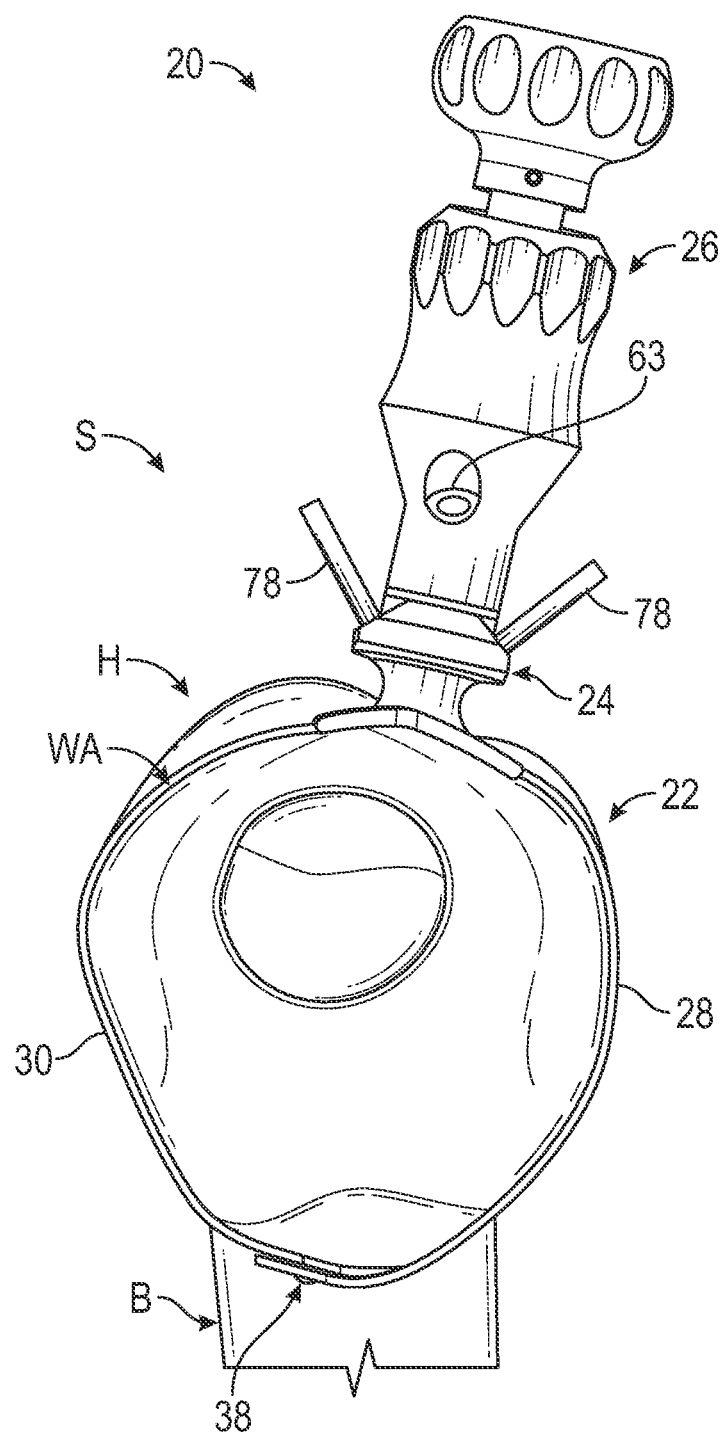
FIG. 17 illustrates another view of the surgical guide positioned relative to the bone of FIG. 16 with the alignment member removed.
Figure 18:
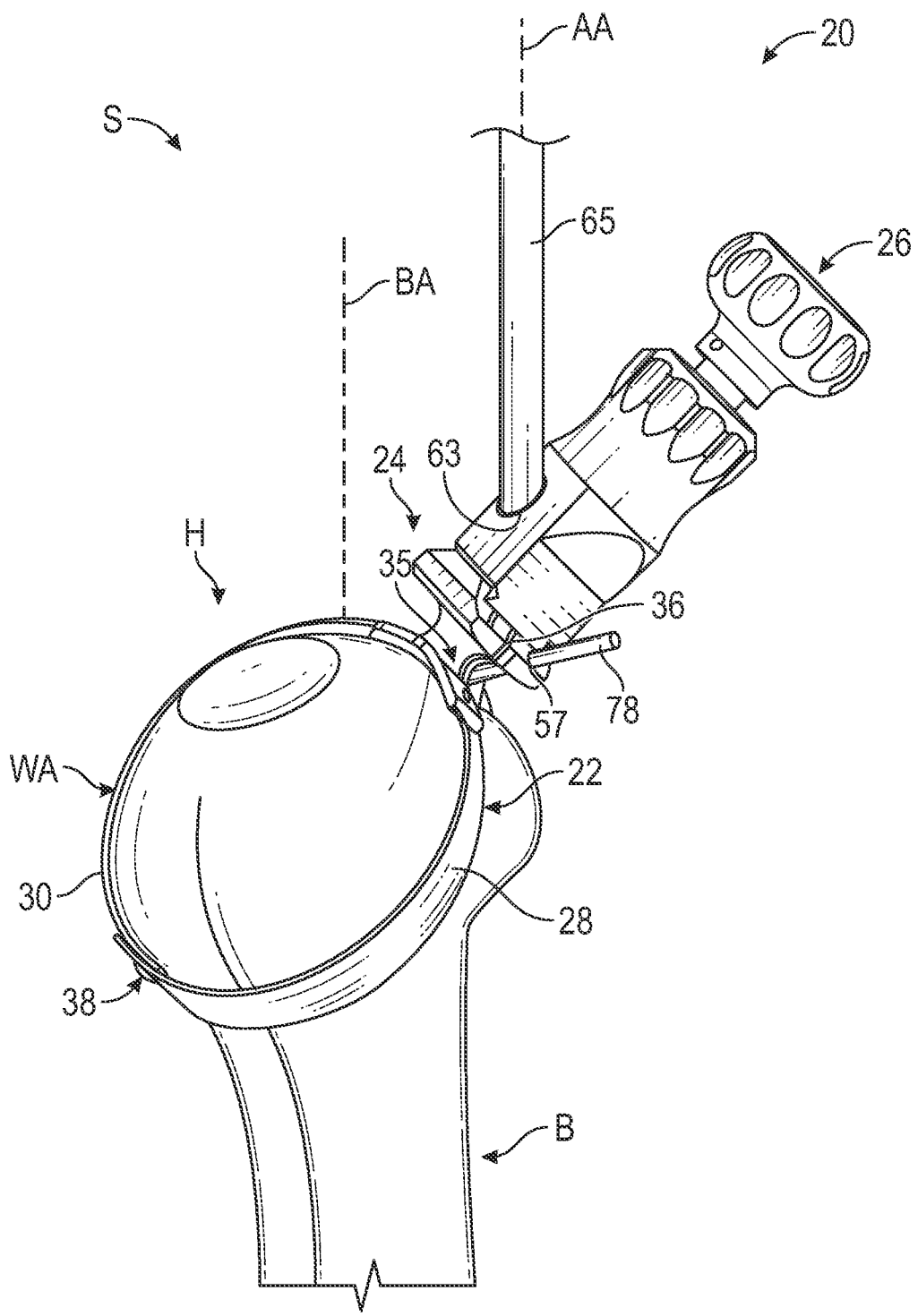
FIG. 18 illustrates a perspective view of the surgical guide and alignment member positioned relative to an axis of the bone of FIG. 16.

Step 80C can include positioning a portion of the bone B in the work area WA at step 80C-3. Step 80C-3 can occur such that the shield 22 at least partially or substantially surrounds a periphery of the bone B, as illustrated in FIGS. 16-18. Positioning the portion of bone B in the work area WA can occur such that the shield 22 and the housing 24 cooperate to substantially surround the periphery of the bone B.

Step 80C can include positioning the surgical guide 20 according to the resection angle α determined at step 80A. Step 80C can include positioning the surgical guide 20 such that the reference plane REF1 associated with the resection slot 36 is substantially parallel to the reference plane REF2.

Step 80C can include aligning the surgical guide 20 with the bone B or another portion of the anatomy at step 80C-4. Step 80C-4 can include inserting an alignment (e.g., inclination) rod 65 into an aperture 63 of the handle 26 (see also FIG. 18). The alignment rod 65 can serve to determine an inclination of the guide 20 relative to the axis BA of the bone B. Step 80C-4 can include moving the surgical guide 20 along the periphery of the bone B to adjust an angle between an axis AA of the alignment rod 65 and the axis BA of the bone B. Step 80C-4 can occur such that the axis AA is substantially parallel to the axis BA.

Figure 19:
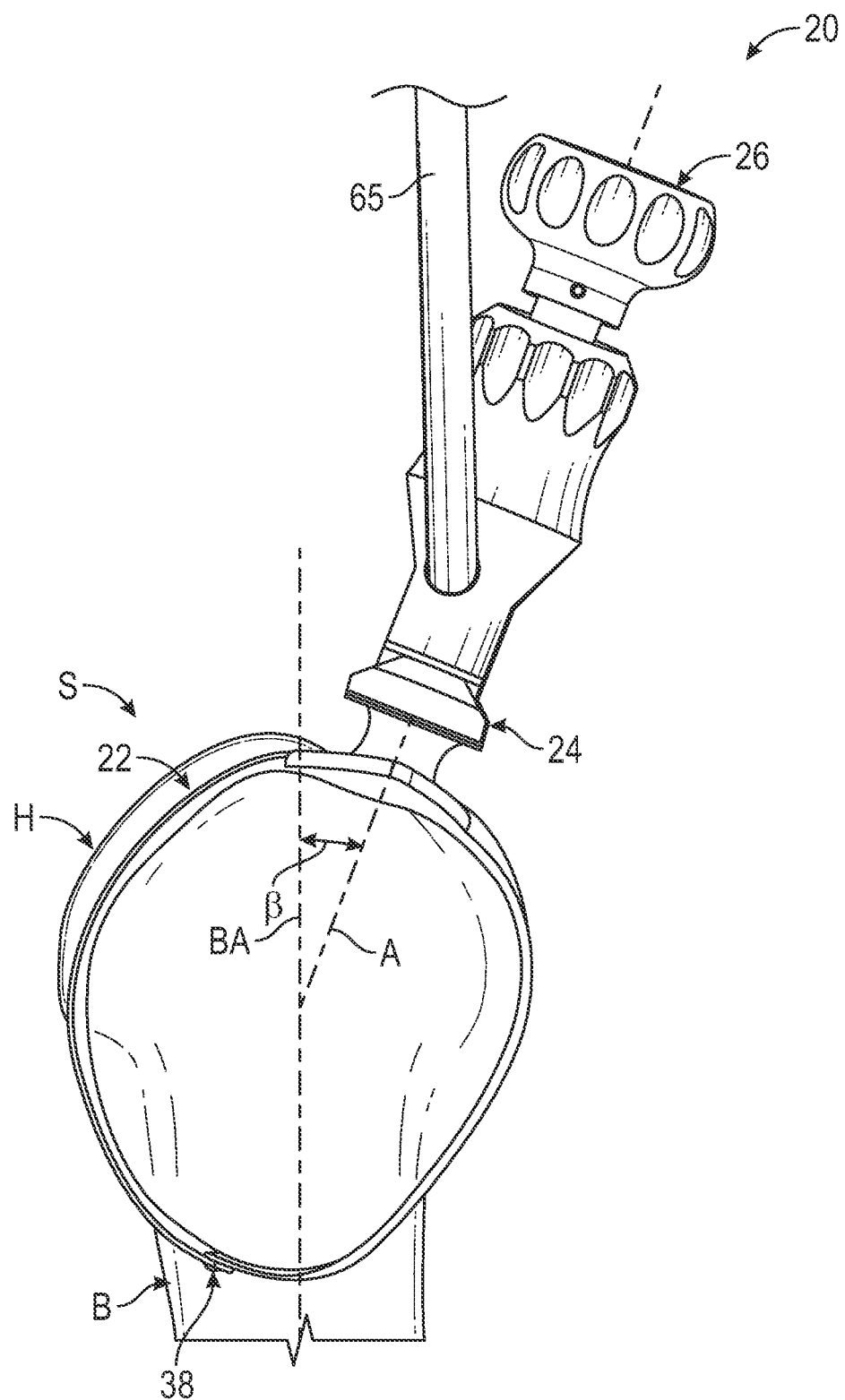
FIG. 19 illustrates another view of the surgical guide positioned at an angle relative to the bone of FIG. 16.

Step 80C can include orienting the axis A of the guide 20 at an angle β relative to the axis BA of the bone B, as illustrated in FIG. 19. The angle β can be established such that the guide 20 is offset from the axis BA of the bone B.

Referring to FIGS. 17-18, with continuing reference to FIG. 12, at step 80D the surgical guide 20 can be secured to the bone B or another portion of the patient anatomy. Step 80D can include inserting one or more fastening elements 78 through respective apertures 57 (FIG. 18) in the housing 24 and then into the bone B to secure the surgical guide 20 at a specified position and orientation relative to the bone B. Step 80D can occur subsequent to aligning the surgical guide 20 at step 80C-4.

Step 80C and/or step 80D can include changing a size of the shield 22 such that the shield 22 substantially conforms to the periphery of the bone B. Changing the size of the shield 22 can include adjusting the connection 38 to move the distal ends of the first and second shield portions 28, 30 relative to each other.

Figure 20:
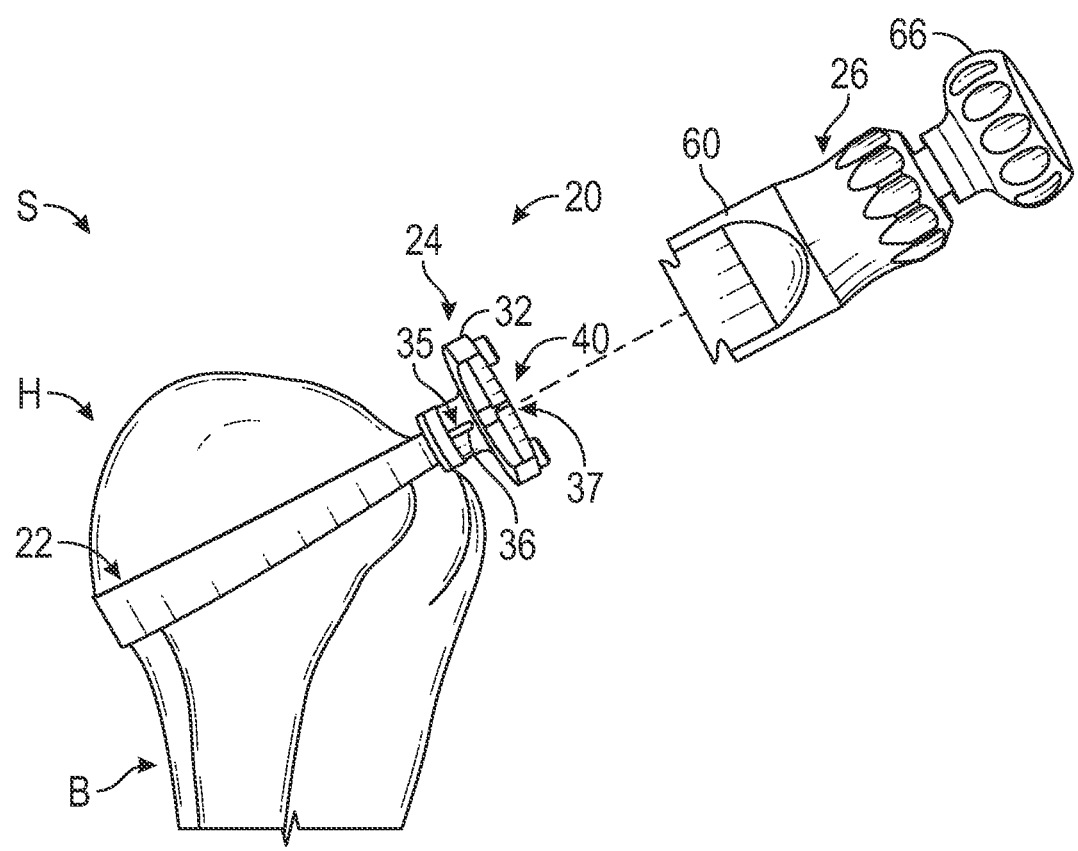
FIG. 20 illustrates the surgical guide of FIG. 16 with a handle removed.

Referring to FIG. 20, with continuing reference to FIG. 12, at step 80E the handle 26 can be removed from the housing 24. Step 80E can occur while a remainder of the surgical guide 20, including the shield 22 and housing 24, are secured to the bone B. Step 80E can include manipulating the control knob 66 to move the actuation member 62 to unlock the handle 26 from the first housing portion 32 of the housing 24 (see FIG. 11B). Step 80E can include moving the handle 26 along the interface 40 to detach the handle 26 from the housing 24 subsequent to unlocking the handle 26. Step 80E can include removing the handle 26 from the surgical site S. Step 80E can occur such that the entrance 37 of the resection slot 36 is uncovered or exposed.

Figure 21:
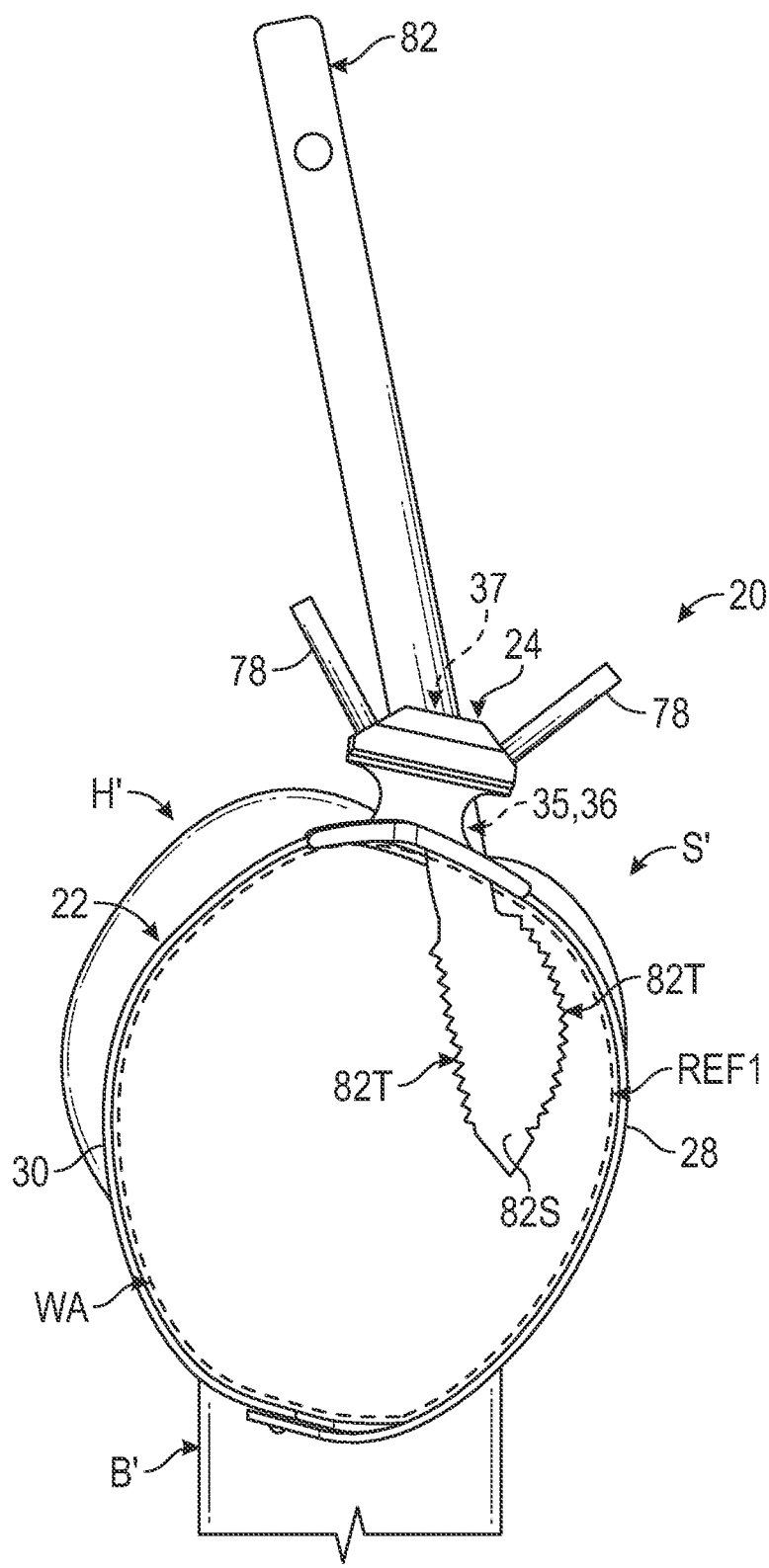
FIG. 21 illustrates a surgical instrument positioned relative to the surgical guide of FIG. 20.

Referring to FIG. 21, with continuing reference to FIG. 12, at step 80F a portion of the bone B' or other tissue can be removed utilizing the surgical guide 20. The portion of the bone B' can include an articular surface and any associated cartilage. Step 80F can include inserting a cutting instrument 82 through the guide passage 35 or resection slot 36 and into the work area WA to resect or otherwise cut the bone B'. The cutting instrument 82 can be a reciprocating bone saw including cutting teeth 82T and a spear tip 82S.

The spear tip 82S can be dimensioned to pierce through cortical bone. Other exemplary cutting instruments include drills, burrs, mills and punches. The surgical guide 20 and one or more cutting instruments 82 can be provided to the surgeon as a kit for an orthopaedic or other surgical procedure. Step 80F can include reciprocating or otherwise moving the cutting instrument 82 along the reference plane REF1 (shown in dashed lines) of the surgical guide 20 to resect or otherwise cut a portion of the bone B' such as the humeral head H'. Inserting the cutting instrument 82 at step 80F can include moving the cutting instrument 82 through the entrance 37 of the resection slot 36 subsequent to detaching the handle 26 at step 80E. The shield 22 can be configured to block movement of the cutting instrument 82 along the reference plane REF1, including outwardly of the periphery of the work area WA. The shield 22 can serve to protect tissue adjacent to the bone B' while resecting or otherwise cutting a portion of the bone B'. The cutting instrument 82 can be removed from the surgical guide 20 and then from the surgical site S.

At step 80G, the surgical guide 20 can be removed from the surgical site S. Step 80G may include moving the surgical guide 20 from the deployed position to the folded position, removing the fastening elements 78 if utilized, and then removing the surgical guide 20 through the access point AP. In implementations, the handle 26 can be attached to the housing 24 to move the surgical guide 20 between the deployed and folded positions and to assist in removing the surgical guide 20.

At step 80H one or more additional procedures may be performed. Step 80H may include positioning an implant or graft along the modified portion of the bone B'. Step 80H may include repairing the access point AP (FIGS. 14-15) and any incisions in the soft tissue.

The novel surgical devices and methods of this disclosure can be incorporated into a practical application by serving to position various surgical instruments at a surgical site during a surgical procedure. The surgical guide may include a shield configured to protect surrounding tissue from contact with the surgical instrument. The surgical guide may be reconfigured to reduce a size of the surgical device during placement in the patient. The disclosed surgical guide can be moved between a folded position and a deployed position. The compact arrangement of the surgical guide may reduce incision sizes and improve patient healing. The surgical guide can include a removable handle, which can further improve a compactness of the surgical guide. The surgical guide can include a lock mechanism to secure the handle to a housing of the surgical guide, which can reduce a likelihood of the handle becoming unsecured from the housing when positioning the surgical guide.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical guide for an orthopaedic procedure comprising:
   a shield including first and second shield portions; and
   a housing including a first housing portion pivotably coupled to a second housing portion; and
   wherein the first and second shield portions are coupled to the respective first and second housing portions, the first and second shield portions are moveable relative to each other between a folded position and a deployed position in response to relative rotation between the first and second housing portions about an axis, the first and second shield portions are configured to bound a work area in the deployed position, the work area is dimensioned to receive a portion of bone, and the housing includes a resection slot extending from the work area.

2. The surgical guide as recited in claim 1, wherein the first shield portion is pivotably coupled to the second shield portion at a connection, and the connection is spaced apart from the housing.

3. The surgical guide as recited in claim 2, wherein the first and second shield portions cooperate with the housing to encircle the work area in the deployed position.

4. The surgical guide as recited in claim 1, further comprising:
   a handle releasably secured to the housing along an interface; and/or
   wherein the resection slot extends between the interface and the work area.

5. The surgical guide as recited in claim 1, wherein the first housing portion includes a first flange extending from a first body, the second housing portion includes a second flange extending from a second body, and the first and second flanges are coupled to the respective first and second shield portions.

6. The surgical guide as recited in claim 5, wherein the first body includes a passageway extending along the resection slot, and the second body includes a pair of lock members configured to deflect inwardly in response to being inserted in the passageway and then to deflect outwardly to lock the second body in the first body.

7. The surgical guide as recited in claim 6, further comprising:
   a handle releasably secured to the housing along an interface; and
   wherein the handle includes an actuation member moveable between first and second positions relative to the interface, the actuation member is configured to engage the lock members in the first position to lock the handle to the housing and is configured to disengage the lock members in the second position such that the handle is releasable from the housing.

8. The surgical guide as recited in claim 1, wherein a first slot extends through the first housing portion, a second slot extends through the second housing portion, and the first and second slots are substantially aligned in the deployed position to establish the resection slot; and/or
   wherein the resection slot is established along the axis.

9. The surgical guide as recited in claim 8, wherein the first slot is transverse to the second slot in response to moving the shield between the deployed position and the folded position.

10. The surgical guide as recited in claim 1, wherein the shield is flexible such that the first and second shield portions are conformable to a periphery of a portion of bone captured in the work area.

11. A kit for an orthopaedic procedure comprising:
a cutting instrument including cutting teeth; and
a surgical guide comprising:
   a shield configured to bound a work area in a deployed position, the work area dimensioned to receive a portion of bone; and
   a housing including first and second housing portions coupled to respective end portions of the shield;
   wherein the first and second housing portions are pivotable relative to each other about an axis to move the shield between a folded position and the deployed position; and
   wherein the housing includes a resection slot extending along a reference plane that intersects the work area, and the shield is configured to block movement of the cutting instrument along the reference plane.

12. The kit as recited in claim 11, wherein the shield includes a first shield portion pivotably coupled to a second shield portion at a connection, and the connection is spaced apart from the housing.

13. The kit as recited in claim 11, wherein a first slot extends through the first housing portion, a second slot extends through the second housing portion, and the first and second slots are substantially aligned along the reference plane in the deployed position to establish the resection slot.

14. The kit as recited in claim 11, further comprising:
a handle releasably secured to the first housing portion along an interface; and
wherein the handle includes an actuation member moveable between first and second positions relative to the interface, the actuation member is configured to engage the second housing portion in the first position to lock the handle to the housing to block access to an entrance to the resection slot, and the actuation member is configured to disengage the second housing portion in the second position such that the handle is releasable from the first housing portion to provide access to the entrance to the resection slot.

15. A method of performing an orthopaedic procedure comprising:
   situating a surgical guide at a surgical site;
   moving the surgical guide from a folded position to a deployed position at the surgical site, wherein the surgical guide comprises:
      a shield configured to bound a work area in the deployed position; and
      a housing including first and second housing portions coupled to respective end portions of the shield;
      wherein the second housing portion is pivotable relative to an axis of the first housing portion to move the shield between the folded position and the deployed position; and
      wherein the housing includes a resection slot extending from the work area;
   positioning a bone in the work area such that the shield at least partially surrounds a periphery of the bone; and
   inserting a cutting instrument through the resection slot and into the work area to resect the bone.

16. The method as recited in claim 15, wherein the step of positioning the bone in the work area occurs such that the shield and the housing cooperate to substantially surround the periphery of the bone.

17. The method as recited in claim 15, wherein the surgical guide includes a handle releasably secured to the first housing portion along an interface, and an entrance to the resection slot is established along the interface, and further comprising:
   moving an actuation member to unlock the handle from the second housing portion, and then moving the handle along the interface to detach the handle from the housing; and
   wherein the step of inserting the cutting instrument includes moving the cutting instrument through the entrance of the resection slot subsequent to detaching the handle.

18. The method as recited in claim 17, further comprising:
inserting an alignment rod into an aperture of the handle; and
moving the surgical guide along the periphery of the bone to adjust an angle between the alignment rod and an axis of the bone, and then inserting one or more fastening elements through the housing and then into the bone to secure the surgical guide.

19. The method as recited in claim 15, wherein the resection slot is established along the axis; and/or
wherein the bone is a humeral head of a humerus.

20. The method as recited in claim 15, further comprising:
moving the surgical guide in the folded position through a soft tissue passage prior to positioning the bone in the work area.

* * * * *